(12) United States Patent
Shuttleworth et al.

(10) Patent No.: US 7,872,003 B2
(45) Date of Patent: Jan. 18, 2011

(54) PHARMACEUTICAL COMPOUNDS

(75) Inventors: Stephen J. Shuttleworth, Slough (GB); Adrian J. Folkes, Slough (GB); Irina S. Chuckowree, Slough (GB); Nan Chi Wan, Slough (GB); Timothy C. Hancox, Slough (GB); Stewart J. Baker, Slough (GB); Sukhjit Sohal, Slough (GB); Mohammed A. Latif, Slough (GB)

(73) Assignee: F. Hoffmann-La Roche AG, Basel (CH)

( * ) Notice: Subject to any disclaimer, the term of this patent is extended or adjusted under 35 U.S.C. 154(b) by 561 days.

(21) Appl. No.: 11/893,625

(22) Filed: Aug. 16, 2007

(65) Prior Publication Data

US 2008/0207609 A1    Aug. 28, 2008

Related U.S. Application Data

(63) Continuation of application No. PCT/GB2005/004146, filed on Oct. 25, 2005.

(51) Int. Cl.
*A61K 31/535* (2006.01)
*C07D 413/14* (2006.01)

(52) U.S. Cl. .................... 514/234.5; 544/116
(58) Field of Classification Search ............. 514/234.5; 544/116
See application file for complete search history.

(56) References Cited

U.S. PATENT DOCUMENTS

| | | | |
|---|---|---|---|
| 3,475,429 A | 10/1969 | Woitun et al. |
| 3,661,908 A | 5/1972 | Woitun et al. |
| 3,763,156 A | 10/1973 | Woitun et al. |
| 3,838,121 A | 9/1974 | Woitun et al. |
| 4,007,187 A | 2/1977 | Fauran et al. |
| 4,146,716 A | 3/1979 | Cox et al. |
| 4,196,207 A | 4/1980 | Webber et al. |
| 6,187,777 B1 | 2/2001 | Norman et al. |
| 6,608,053 B2 | 8/2003 | Hayakawa et al. |
| 6,838,457 B2 | 1/2005 | Hayakawa et al. |
| 7,037,915 B2 | 5/2006 | Hayakawa et al. |
| 7,173,029 B2 | 2/2007 | Hayakawa et al. |
| 2003/0220365 A1 | 11/2003 | Stewart et al. |

FOREIGN PATENT DOCUMENTS

| | | |
|---|---|---|
| EP | 1277738 A1 | 1/2003 |
| GB | 1393161 | 5/1975 |
| WO | WO 2004/017950 A2 | 3/2004 |
| WO | WO 2004/065391 A1 | 8/2004 |
| WO | WO 2006/046031 A1 | 5/2006 |
| WO | WO 2006/046035 A1 | 5/2006 |

OTHER PUBLICATIONS

Cancer and Metastasis Reviews (1998), 17(1), 91-106.*
Science (1999), vol. 286, 531-537.*
International Search Report and Written Opinion of the International Searching Authority, PCT/GB2005/004146, Mar. 21, 2006.
Manhas et al., "Heterocyclic Compounds. V. 2, 4-Disubstituted Thienopyrimidones (1)", Journal of Heterocyclic Chemistry, 13, 633-638, 1976.

* cited by examiner

*Primary Examiner*—Rebecca L Anderson
(74) *Attorney, Agent, or Firm*—Viksnins, Harris & Padys PLLP

(57) ABSTRACT

Fused pyrimidines of formula (I):

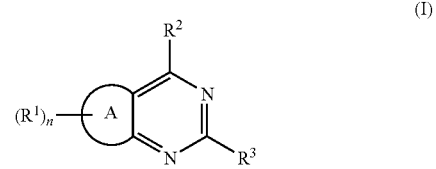

wherein $R^1$-$R^3$, A and n have any of the values described in the specification; and pharmaceutically acceptable salts thereof; have activity as inhibitors of PI3K and may thus be used to treat diseases and disorders arising from abnormal cell growth, function or behavior associated with PI3 kinase such as cancer, immune disorders, cardiovascular disease, viral infection, inflammation, metabolism/endocrine disorders and neurological disorders. Processes for synthesizing the compounds are also described.

11 Claims, No Drawings

PHARMACEUTICAL COMPOUNDS

PRIORITY OF THE INVENTION

This application is a Continuation of PCT/GB2005/004146, filed Oct. 25, 2005, which claims priority from UK Application No. 0423653.5, filed Oct. 25, 2004, which applications are incorporated herein by reference.

FIELD OF THE INVENTION

The present invention relates to pyrimidine derivatives and their use as inhibitors of phosphatidylinositol 3-kinase (PI3K).

BACKGROUND TO THE INVENTION

Phosphatidylinositol (hereinafter abbreviated as "PI") is one of a number of phospholipids found in cell membranes. In recent years it has become clear that PI plays an important role in intracellular signal transduction. In the late 1980s, a PI3 kinase (PI3K) was found to be an enzyme which phosphorylates the 3-position of the inositol ring of phosphatidylinositol (D. Whitman et al, 1988, Nature, 332, 664).

PI3K was originally considered to be a single enzyme, but it has now been clarified that a plurality of subtypes are present in PI3K. Each subtype has its own mechanism for regulating activity. Three major classes of PI3Ks have been identified on the basis of their in vitro substrate specificity (B. Vanhaesebroeck, 1997, Trend in Biol. Sci, 22, 267). Substrates for class I PI3Ks are PI, PI 4-phosphate (PI4P) and PI 4,5-biphosphate (PI (4,5)P2). Class I PI3Ks are further divided into two groups, class Ia and class Ib, in terms of their activation mechanism. Class Ia PI3Ks include PI3K p110α, p110β and p110δ subtypes, which transmit signals from tyrosine kinase-coupled receptors. Class Ib PI3K includes a p110γ subtype activated by a G protein-coupled receptor. PI and PI(4)P are known as substrates for class II PI3Ks. Class II PI3Ks include PI3K C2α, C2β and C2γ subtypes, which are characterized by containing C2 domains at the C terminus. The substrate for class III PI3Ks is PI only.

In the PI3K subtypes, the class Ia subtype has been most extensively investigated to date. The three subtypes of class Ia are heterodimers of a catalytic 110 kDa subunit and regulatory subunits of 85 kDa or 55 kDa. The regulatory subunits contain SH2 domains and bind to tyrosine residues phosphorylated by growth factor receptors with a tyrosine kinase activity or oncogene products, thereby inducing the PI3K activity of the p110 catalytic subunit which phosphorylates its lipid substrate. Thus, the class Ia subtypes are considered to be associated with cell proliferation and carcinogenesis.

WO 01/083456 describes a series of condensed heteroaryl derivatives which have activity as inhibitors of PI3K and which suppress cancer cell growth.

SUMMARY OF THE INVENTION

It has now been found that a novel class of fused pyrimidine compounds are effective inhibitors of PI3K with drug-like physicochemical and pharmacokinetic properties. The compounds exhibit selectivity for class Ia PI3Ks over class Ib.

Accordingly, the present invention provides a compound which is a fused pyrimidine of formula (I):

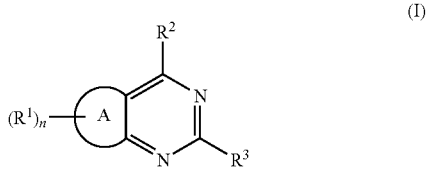

wherein

A represents a thiophene or furan ring;

n is 1 or 2;

$R^1$ is a group of formula:

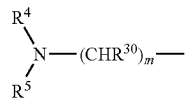

wherein m is 0 or 1;

$R^{30}$ is H or $C_1$-$C_6$ alkyl;

$R^4$ and $R^5$ form, together with the N atom to which they are attached, a 5- or 6-membered saturated N-containing heterocyclic group which includes 0 or 1 additional heteroatoms selected from N, S and O, which may be fused to a benzene ring and which is unsubstituted or substituted; or one of $R^4$ and $R^5$ is alkyl and the other is a 5- or 6-membered saturated N-containing heterocyclic group as defined above or an alkyl group which is substituted by a 5- or 6-membered saturated N-containing heterocyclic group as defined above;

$R^2$ is selected from:

wherein $R^6$ and $R^7$ form, together with the nitrogen atom to which they are attached, a morpholine, thiomorpholine, piperidine, piperazine, oxazepane or thiazepane group which is unsubstituted or substituted; and

wherein Y is a $C_2$-$C_4$ alkylene chain which contains, between constituent carbon atoms of the chain and/or at one or both ends of the chain, 1 or 2 heteroatoms selected from O, N and S, and which is unsubstituted or substituted;

and $R^3$ is selected from:
(a) a group of the following formula:

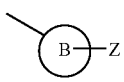

wherein B is a phenyl ring which is unsubstituted or substituted and Z is selected from H, —OR, —SR, $CH_2OR$, —$CO_2R$, $CF_2OH$, $CH(CF_3)OH$, $C(CF_3)_2OH$, —$(CH_2)_qOR$, —$(CH_2)_qNR_2$, —$C(O)N(R)_2$, —$NR_2$, —$NRC(O)R$, —$S(O)_m N(R)_2$, —$OC(O)R$, $OC(O)N(R)_2$, —$NRS(O)_mR$, —$RC(O)N(R)_2$, CN, halogen and —$NO_2$, wherein each R is independently selected from H, $C_1$-$C_6$ alkyl, $C_3$-$C_{10}$ cycloalkyl and a 5- to 12-membered aryl or heteroaryl group, the group being unsubstituted or substituted, m is 1 or 2 and q is 0, 1 or 2;

(b) a heteroaryl group which contains 1, 2, 3 or 4 ring nitrogen atoms and 0, 1 or 2 additional heteroatoms selected from O and S, which group is monocyclic or bicyclic and which is unsubstituted or substituted; and (c) a group comprising a benzene ring which is unsubstituted or substituted and which is fused to a heteroaryl group as defined above;

provided that $R^3$ is not an indole group or an indazole group, which group is unsubstituted or substituted;

or a pharmaceutically acceptable salt thereof.

DETAILED DESCRIPTION OF THE INVENTION

The thiophene or furan ring A in formula (I) adopts either of the two available regiochemical orientations. Formula (I) thus covers the thieno[3,2-d]pyrimidines and furano[3,2-d]pyrimidines of the following formula (Ia) as well as the thieno[2,3-d]pyrimidines and furano[2,3-d]pyrimidines of the following formula (Ib):

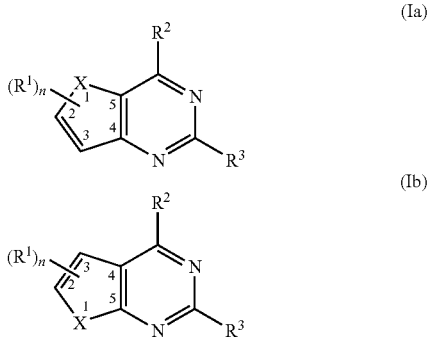

wherein each of $R^1$ to $R^3$ and n is as defined above and X is S or O.

In formula (I), the group or groups $R^1$, which are the same or different in a given compound when n is 2, may be bonded to either or both of the two available ring positions on the thiophene or furan ring A. Referring to structures (Ia) and (Ib) above, therefore, when n is 1 the furan or thiophene ring is mono-substituted by $R^1$ at the 2-position or the 3-position. When n is 2, the thiophene or furan ring is di-substituted by $R^1$ at positions 2 and 3.

As specified herein, an alkyl group is a straight or branched chain saturated hydrocarbon radical which is unsubstituted or substituted. Typically it is $C_1$-$C_{20}$ alkyl, for instance $C_1$-$C_{10}$ alkyl, such as $C_1$-$C_6$ alkyl or $C_1$-$C_4$ alkyl, for example methyl, ethyl, i-propyl, n-propyl, t-butyl, s-butyl or n-butyl. It may also be pentyl, hexyl, heptyl, octyl and the various branched chain isomers thereof.

When an alkyl group is substituted it typically bears one or more substituents $R^{20}$ selected from halogen, alkoxy, carbocyclyl, a 5- or 6-membered saturated N-containing heterocyclic group as defined above, OH, SR, CN, nitro, $NR_2$, —COOR, —C(O)R, $S(O)_mR$ and —$CONR_2$, wherein each R is H, unsubstituted alkyl or $C_3$-$C_{10}$ cycloalkyl and m is 1 or 2. It is, for instance, a haloalkyl group or a group -alk-$N(R^4)(R^5)$ wherein alk is an alkylene chain and $R^4$ and $R^5$ form, together with the N atom to which they are attached, a 5- or 6-membered saturated N-containing heterocyclic group which includes 0 or 1 additional heteroatoms selected from N, S and O, which may be fused to a benzene ring and which is unsubstituted or substituted. Typically $R^{20}$ is selected from halogen, alkoxy, carbocyclyl, a 5- or 6-membered saturated N-containing heterocyclic group as defined above, OH, CN, $NR_2$, —COOR and —$CONR_2$, wherein each R is H or unsubstituted alkyl as defined above. It is, for instance, a haloalkyl group or a group -alk-$N(R^6)(R^5)$ wherein alk is an alkylene chain and $R^4$ and $R^5$ form, together with the N atom to which they are attached, a 5- or 6-membered saturated N-containing heterocyclic group as defined above.

An alkylene group is unsubstituted or substituted, straight or branched chain saturated divalent hydrocarbon group. Typically it is $C_1$-$C_8$ alkylene, for instance $C_1$-$C_6$ alkylene. Preferably it is $C_1$-$C_4$ alkylene, for example $C_2$-$C_4$ alkylene, such as methylene, ethylene, i-propylene, n-propylene, t-butylene, s-butylene or n-butylene. It may also be pentylene, hexylene, heptylene, octylene and the various branched chain isomers thereof. When the alkylene group is substituted it is typically substituted by a group $R^{20}$ as defined above.

An alkenyl group is an unsubstituted or substituted, straight or branched chain hydrocarbon radical having one or more double bonds. Typically it is $C_2$-$C_8$ alkenyl, for instance $C_2$-$C_6$ alkenyl, such as allyl, butenyl, butadienyl, pentenyl or hexenyl. When the alkenyl group is substituted it is typically substituted by a group $R^{20}$ as defined above or by alkyl which is unsubstituted or substituted by a group $R^{20}$ as defined above.

An alkynyl group is an unsubstituted or substituted, straight or branched chain hydrocarbon radical having one or more triple bonds. Typically it is $C_2$-$C_8$ alkynyl, for instance $C_2$-$C_6$ alkynyl, such as ethynyl, propynyl or butynyl. When the alkynyl group is substituted it is typically substituted by a group $R^{20}$ as defined above or by alkyl which is unsubstituted or substituted by a group $R^{20}$ as defined above.

A haloalkyl group is an alkyl group as defined above, substituted by one or more halogen atoms. It can be a perhaloalkyl group, for instance trifluoromethyl or perfluorohexyl.

A halogen is chlorine, fluorine, bromine or iodine. It is typically bromine or iodine.

An alkoxy group is typically $C_1$-$C_6$ alkoxy, for instance $C_1$-$C_4$ alkoxy, such as methoxy, ethoxy, i-propoxy, n-propoxy, t-butoxy, n-butoxy or s-butoxy. It is unsubstituted or substituted, for instance by a group $R^{20}$ as defined above or by alkyl which is unsubstituted or substituted by a group $R^{20}$ as defined above or by alkyl which is unsubstituted or substituted by a group $R^{20}$ as defined above. Typically it is substituted by carbocyclyl, morpholino, OH, CN, $NR_2$, —COOR or —$CONR_2$, wherein each R is H or unsubstituted alkyl as defined above.

A carbocyclyl group is a non-aromatic saturated or unsaturated monocyclic hydrocarbon ring, typically having from 3 to 10 carbon atoms. It may be a $C_3$-$C_8$ cycloalkyl group, or $C_5$-$C_{10}$ cycloalkyl group, for instance cyclopropyl, cyclobutyl, cyclopentyl, cyclohexyl, cycloheptyl or cyclooctyl. Alternatively it may be a cycloalkenyl group, typically $C_4$-$C_8$ cycloalkenyl, for instance cyclopentenyl, cyclohexenyl, cyclohexadienyl, cycloheptenyl, cycloheptadienyl, cyclooctenyl or cyclooctadienyl. A carbocyclyl group may be unsubstituted or substituted, for instance by a group $R^{20}$ as defined above or by alkyl which is unsubstituted or substituted by a group $R^{20}$ as defined above. Typically it is substituted by alkoxy, morpholino, OH, CN, $NR_2$, —COOR and —$CONR_2$, wherein each R is H or unsubstituted alkyl as defined above.

A 5- or 6-membered saturated N-containing heterocyclic group which includes 0 or 1 additional heteroatoms selected from N, S and O, which may be fused to a benzene ring and which is unsubstituted or substituted is typically selected from morpholine, piperidine, piperazine, pyrrolidine, thiomorpholine, quinoline, isoquinoline, diazepane, oxazepane and thiazepane.

When a 5- or 6-membered saturated N-containing heterocyclic group as defined above is substituted it is typically substituted by one or more substituents, for instance 1, 2 or 3 substituents, typically by 1 or 2 substituents. Typically the substituents are selected from alkyl which is unsubstituted or substituted, alkoxy which is unsubstituted or substituted, —$NR_2$, —N(R''')-alk-OR, -alk-OR, —O-alk-OR, -alk-C(O)$NR_2$, —C(O)$NR_2$, -alk-Het, —N(R)-Het, —O-Het, —N(R)—C(O)-alk-OR, —C(O)—N(R)-alk-OR, -alk-S(O)$_2$R, —N(R)-alk-OR, -alk-NR'R", —N(R''')—S(O)$_2$R, S(O)$_2$R''', -alk-N(R)-alk-OR, —S(O)$_2$-alk-OR, a second 5- or 6-membered saturated N-containing heterocyclic group as defined above, a 5- or 6-membered N-containing heteroaryl group which is unsubstituted or substituted and which may be fused to a benzene ring, —COOR, —$CONR_2$, oxo (=O), —$SO_2NR_2$, —$SO_2$-alk-$NR_2$ and —CO-alk-OR, wherein: alk is an alkylene chain as defined above; Het is a 5- or 6-membered N-containing heteroaryl group as defined herein which is unsubstituted or substituted; R is H or alkyl, or when two groups R are bonded to N they may form, together with the N atom, a saturated 5- or 6-membered N-containing heterocyclic group as defined herein which is unsubstituted or substituted; each of R' and R" is independently H, alkyl or alkoxy; and R''' is alkyl which is unsubstituted or substituted, for instance by $CF_3$, $NR_2$, OR, a 5- or 6-membered saturated N-containing heterocyclic group as defined herein or a 5- or 6-membered N-containing heteroaryl group as defined herein, the said heterocyclic and heteroaryl groups being unsubstituted or substituted. It may be substituted by a group $R^{20}$ as defined above or by alkyl which is unsubstituted or substituted by a group $R^{20}$ as defined above.

Typically a 5- or 6-membered saturated N-containing heterocyclic group as defined above is substituted by a group selected from alkyl which is unsubstituted or substituted, alkoxy which is unsubstituted or substituted, a second 5- or 6-membered saturated N-containing heterocyclic group as defined above, a 5- or 6-membered N-containing heteroaryl group which is unsubstituted or substituted and which may be fused to a benzene ring, —COOR, —$CONR_2$, —CONR, oxo (=O), OH, —$NSO_2R$, —$SO_2NR_2$ or —CO(CH$_2$)$_n$OR wherein R is H or alkyl, —NR'R" wherein each of R' and R" is independently H, alkyl or alkoxy, and —$SO_2R'''$ wherein R''' is alkyl which is unsubstituted or substituted, for instance by $NR_2$ or a 5- or 6-membered saturated N-containing heterocyclic group as defined above.

More typically a 5- or 6-membered saturated N-containing heterocyclic group is substituted by one or more substituents selected from alkyl as defined above which is unsubstituted or substituted (for instance by $R^{20}$ as defined above), haloalkyl as defined above, alkoxy as defined above which is unsubstituted or substituted, halogen, hydroxy, CN, nitro, amino, oxo (=O), and —NR'R" wherein each of R' and R" is independently H or alkyl.

A 5-, 6- or 7-membered saturated heterocyclic group which contains 1 or 2 heteroatoms selected from N, S and O and which is unsubstituted or substituted is typically selected from tetrahydropyran, tetrahydrothiopyran, tetrahydrofuran and tetrahydrothiofuran.

When a 5-, 6- or 7-membered saturated heterocyclic group which contains 1 or 2 heteroatoms selected from N, S and O is substituted it may be substituted as specified above for a 5- or 6-membered saturated N-containing heterocyclic group.

A heteroaryl group is a heteroaryl group which contains 1, 2 3 or 4 ring nitrogen atoms and 0, 1 or 2 additional heteroatoms selected from O, N and S, which group is monocyclic or bicyclic and which is unsubstituted or substituted. It is typically a 5- to 12-membered ring. Examples of a heteroaryl group include pyrrole, pyrazole, triazole, tetrazole, indazole, thiazole, isothiazole, oxazole, isooxazole, indole, isoindole, 1,3-dihydro-indol-2-one, pyridine-2-one, pyridine, pyridin-3-ol, imidazole, 1,3-dihydro-benzimidazolone, benzimidazole, benzothiazole, benzothiadiazole, quinoline, isoquinoline, quinoxaline, pyrazolopyridine, aminopyrazolinone, imidazopyridine, pyrimidine, pyridazine, pyrazine and isatin groups. Preferred examples include indazole, indole, pyrazole and tetrazole groups. These groups may be unsubstituted or substituted, for instance by a group $R^{20}$ as specified above or by alkyl which is unsubstituted or substituted by a group $R^{20}$ as defined above.

A 5- or 6-membered N containing heteroaryl group which may be fused to a benzene ring is typically selected from pyrrole, pyrazole, triazole, tetrazole, indazole, thiazole, isothiazole, oxazole, isooxazole, indole, isoindole, 1,3-dihydro-indol-2-one, pyridine-2-one, pyridine, pyridin-3-ol, imidazole, 1,3-dihydro-benzimidazolone, benzimidazole, benzothiazole, benzothiadiazole, quinoline, isoquinoline, quinoxaline, pyrazolopyridine, aminopyrazolinone, imidazopyridine, pyrimidine, pyridazine and pyrazine. When such a heteroaryl group is substituted it may be substituted by a group $R^{20}$ as defined above or by alkyl which is unsubstituted or substituted by a group $R^{20}$ as defined above.

In $R^1$, m is 0 or 1, typically 1. $R^{30}$ is typically H. $R^4$ and $R^5$ typically form, together with the N atom to which they are attached, a saturated N-containing heterocyclic group selected from morpholine, thiomorpholine, piperidine, piperazine, pyrrolidine, quinoline, isoquinoline, diazepane, oxazepane and thiazepane. The heterocyclic group formed by $R^4$ and $R^5$ is unsubstituted or substituted, for instance by the examples of substituent groups listed above, such as a group $R^{20}$ as defined above or by alkyl which is unsubstituted or substituted by a group $R^{20}$ as defined above.

In definition (a) of $R^2$ in formula (I), the ring formed by $R^6$ and $R^7$ is typically morpholine which is unsubstituted or substituted, for instance by a group $R^{20}$ as specified above or by alkyl which is unsubstituted or substituted by a group $R^{20}$ as defined above. It may alternatively be a group selected from tetrahydropyran, tetrahydrothiopyran, tetrahydrofuran and tetrahydrothiofuran, each of which is unsubstituted or substituted, for instance, for instance by a group $R^{20}$ as specified above or by alkyl which is unsubstituted or substituted by a group $R^{20}$ as defined above. When the ring formed by $R^6$ and $R^7$ is substituted it may be substituted on either a ring heteroatom or a ring carbon atom, for instance by a group $R^{20}$ as defined above.

In definition (b) of $R^2$ in formula (I), the alkylene chain represented by Y forms, together with the carbon atoms to which it is attached, a saturated 5-, 6- or 7-membered heterocyclic ring which contains 1 or 2 heteroatoms selected from O, N and S and which is unsubstituted or substituted. Examples of the heterocyclic ring include tetrahydropyran, tetrahydrofuran, tetrahydrothiopyran, tetrahydrothiofuran and morpholine. When the heterocyclic ring is substituted it is typically substituted by one or more substituents, for instance 1, 2 or 3 substituents, selected from halogen, alkyl, haloalkyl (for instance trifluoromethyl), alkoxy, OH, CN, $NR_2$, oxo (=O), —COOR and —$CONR_2$, wherein each R is H or unsubstituted alkyl as defined above.

In the definition (a) for $R^3$ the phenyl ring B is unsubstituted (apart from group Z) or substituted. When it is unsubstituted the group Z is the sole substituent. When it is substituted it typically comprises, in addition to group Z, one or more substituents selected from halo, alkyl, alkenyl, alkynyl, CN, $NO_2$, OR', SR', $NR'_2$, C(O)R', SOR', $SO_2R'$, $SO_2NR'_2$, NC(O)R' and $CO_2R'$, wherein each R' is independently H or $C_1$-$C_6$ alkyl.

Group Z is bonded to any available ring position on the phenyl ring B. Thus it may be situated at the 2-, 3-, 4-, 5- or 6-position of the phenyl ring. Typically it is bonded at position 3 or 4. Z is most typically other than H, such that moiety —BZ is a substituted phenyl ring. A typical example of Z is a group OR as defined above, in particular OH. In this embodiment the OR group, or OH group, is typically bonded at ring position 3 or 4 of phenyl ring B. Typically —BZ is a 3-hydroxyphenyl or 4-hydroxyphenyl group, or an isostere thereof, other than an indole or indazole group which is unsubstituted or substituted.

An isostere as used herein is a functional group which possesses binding properties which are the same as, or similar to, the 3-hydroxyphenyl or 4-hydroxyphenyl group in the context of the structure of formula (I). Isosteres of 3-hydroxyphenyl and 4-hydroxyphenyl groups are encompassed within definitions (b) and (c) above for $R^3$.

In definition (b) for $R^3$ the heteroaryl group is unsubstituted or substituted. If it is substituted it may be substituted by one or more substituents selected from a group Z, $R^{20}$ as defined above, alkyl which is unsubstituted or substituted by a $R^{20}$ as defined above, any group specified above as an additional substituent on the phenyl ring B, and an oxo group (=O). Typically, if substituted, the heteroaryl group is substituted by OH, $NH_2$ or an oxo group. In one embodiment the heteroaryl group is unsubstituted.

In definition (c) for $R^3$ the benzene ring is unsubstituted or substituted. If it is substituted it may be substituted by one or more substituents selected from a group Z, $R^{20}$ as defined above, alkyl which is unsubstituted or substituted by $R^{20}$ as defined above, and any of the groups specified above as an additional substituent on the phenyl ring B. The heteroaryl group to which the benzene ring is fused is itself unsubstituted or substituted, for instance by a group Z, $R^{20}$ or alkyl which is unsubstituted or substituted by a group $R^{20}$ as defined above; by any group specified above as an option for an additional substituent on the phenyl ring B; or by an oxo group (=O). In one embodiment both the benzene ring and the heteroaryl group are unsubstituted.

Examples of the groups included in definitions (b) and (c) for $R^3$ include pyrrole, pyrazole, triazole, tetrazole, thiazole, isothiazole, oxazole, isooxazole, isoindole, 1,3-dihydro-indol-2-one, pyridine-2-one, pyridine, pyridin-3-ol, imidazole, 1,3-dihydro-benzimidazolone, benzimidazole, benzothiazole, benzothiadiazole, quinoline, isoquinoline, quinoxaline, pyrazolopyridine, aminopyrazolinone, imidazopyridine, pyrimidine, pyridazine, pyrazine and isatin groups. Preferred examples include pyrazole and tetrazole groups. These groups may be unsubstituted or substituted, for instance by a group Z, $R^{20}$ or alkyl which is unsubstituted or substituted by a group $R^{20}$ as defined above. Typically these groups are isosteres.

More specifically, groups included in definitions (b) and (c) for $R^3$ as defined above include the following structures, which are typically isosteres as defined above:

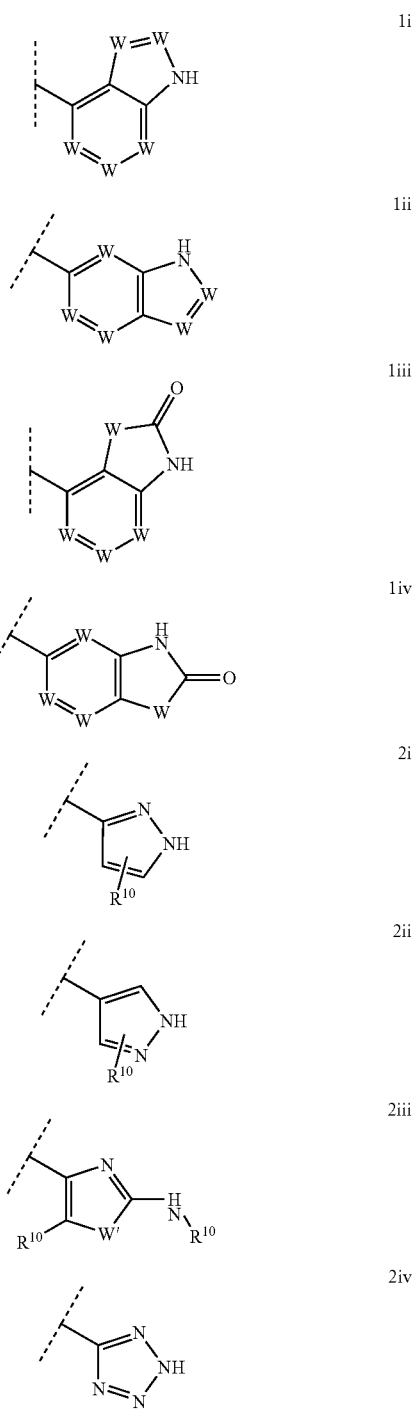

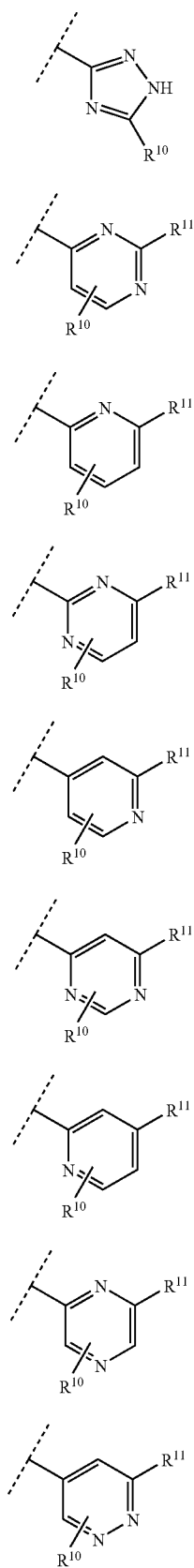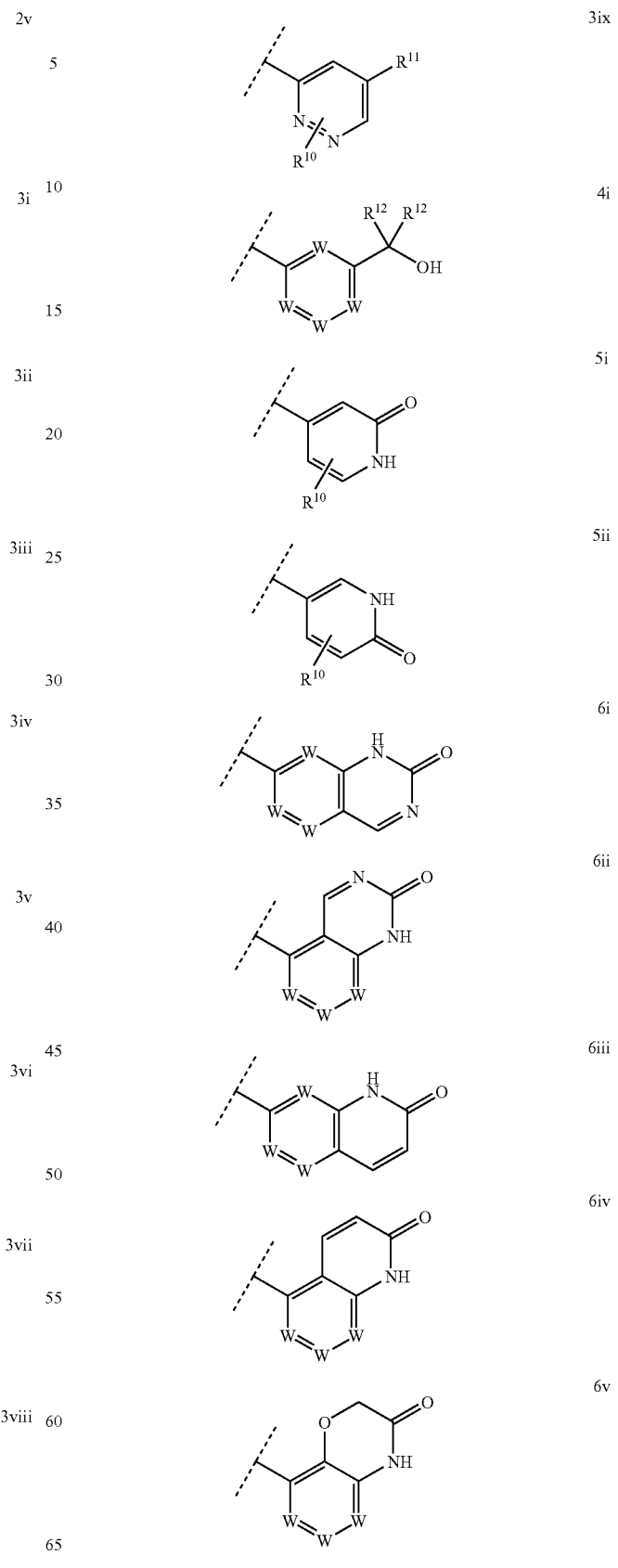

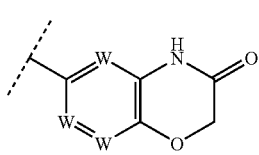

wherein each $R^{10}$ is independently selected from H, $C_1$-$C_6$ alkyl, $C_1$-$C_6$ alkoxy, $C_1$-$C_6$ acyl, —C(O)NR'R", —S(O)$_t$NR'R", aryl, heteroaryl, sulphonyl and halogen, wherein R' and R" are each independently H or $C_1$-$C_6$ alkyl and t is 1 or 2;

each $R^{11}$ is independently selected from —OR$^{10}$ and —N(R$^{10}$)$_2$, wherein $R^{10}$ is as defined above;

each $R^{12}$ is independently H, F or CF$_3$;

each W is independently selected from CR$^{10}$ and N, wherein $R^{10}$ is as defined above;

and W' is selected from O, S and NR$^{12}$ wherein $R^{12}$ is as defined above.

with the proviso that formulae (1i) and (1ii) are other than indole and indazole.

Specific examples of compounds of the invention include:

3-(4-Morpholin-4-yl-6-morpholin-4-ylmethyl-thieno[3,2-d]pyrimidin-2-yl)-phenol;
3-(4-Morpholin-4-yl-6-pyrrolidin-1-ylmethyl-thieno[3,2-d]pyrimidin-2-yl)-phenol;
3-[6-(4-Methyl-piperazin-1-ylmethyl)-4-morpholin-4-yl-thieno[3,2-d]pyrimidin-2-yl]-phenol;
3-[6-(6,7-Dimethoxy-3,4-dihydro-1H-isoquinolin-2-ylmethyl)-4-morpholin-4-yl-thieno[3,2-d]pyrimidin-2-yl]-phenol;
3-(6-[1,4']Bipiperidinyl-1'-ylmethyl-4-morpholin-4-yl-thieno[3,2-d]pyrimidin-2-yl)-phenol;
3-[4-Morpholin-4-yl-6-(4-pyrimidin-2-yl-piperazin-1-ylmethyl)-thieno[3,2-d]pyrimidin-2-yl]-phenol;
3-[6-(4-Cyclohexylmethyl-piperazin-1-ylmethyl)-4-morpholin-4-yl-thieno[3,2-d]pyrimidin-2-yl]-phenol;
4-[2-(3-Hydroxy-phenyl)-4-morpholin-4-yl-thieno[3,2-d]pyrimidin-6-ylmethyl]-piperazine-1-carboxylic acid tert-butyl ester;
3-(4-Morpholin-4-yl-6-piperazin-1-ylmethyl-thieno[3,2-d]pyrimidin-2-yl)-phenol trifluoroacetic acid salt;
3-{6-[4-(2-Methoxy-ethyl)-piperazin-1-ylmethyl]-4-morpholin-4-yl-thieno[3,2-d]pyrimidin-2-yl}-phenol;
3-[6-(4-Methyl-[1,4]diazepan-1-ylmethyl)-4-morpholin-4-yl-thieno[3,2-d]pyrimidin-2-yl]-phenol;
{4-[2-(3-Hydroxy-phenyl)-4-morpholin-4-yl-thieno[3,2-d]pyrimidin-6-ylmethyl]-piperazin-1-yl}-acetic acid ethyl ester;
1-{4-[2-(3-Hydroxy-phenyl)-4-morpholin-4-yl-thieno[3,2-d]pyrimidin-6-ylmethyl]-piperazin-1-yl}-ethanone;
3-{6-[4-(2-Hydroxy-ethyl)-piperazin-1-ylmethyl]-4-morpholin-4-yl-thieno[3,2-d]pyrimidin-2-yl}-phenol;
3-(4-Morpholin-4-yl-6-thiomorpholin-4-ylmethyl-thieno[3,2-d]pyrimidin-2-yl)-phenol;
3-[6-(4-Ethyl-piperazin-1-ylmethyl)-4-morpholin-4-yl-thieno[3,2-d]pyrimidin-2-yl]-phenol;
3-(6-{[Methyl-(1-methyl-piperidin-4-yl)-amino]-methyl}-4-morpholin-4-yl-thieno[3,2-d]pyrimidin-2-yl)-phenol;
3-[6-(4-Dimethylamino-piperidin-1-ylmethyl)-4-morpholin-4-yl-thieno[3,2-d]pyrimidin-2-yl]-phenol;
4-[2-(3-Hydroxy-phenyl)-4-morpholin-4-yl-thieno[3,2-d]pyrimidin-6-ylmethyl]-piperazin-2-one;
3-[6-(4-Methanesulfonyl-piperazin-1-ylmethyl)-4-morpholin-4-yl-thieno[3,2-d]pyrimidin-2-yl]-phenol;
{4-[2-(3-Hydroxy-phenyl)-4-morpholin-4-yl-thieno[3,2-d]pyrimidin-6-ylmethyl]-piperazin-1-yl}-acetonitrile;
3-[4-Morpholin-4-yl-6-(4-morpholin-4-yl-piperidin-1-ylmethyl)-thieno[3,2-d]pyrimidin-2-yl]-phenol;
3-[6-(4-Amino-piperidin-1-ylmethyl)-4-morpholin-4-yl-thieno[3,2-d]pyrimidin-2-yl]-phenol;
3-[6-(3-Dimethylamino-pyrrolidin-1-ylmethyl)-4-morpholin-4-yl-thieno[3,2-d]pyrimidin-2-yl]-phenol;
1-[2-(3-Hydroxy-phenyl)-4-morpholin-4-yl-thieno[3,2-d]pyrimidin-6-ylmethyl]-4-morpholin-4-ylmethyl-piperidin-4-ol;
4-[2-(3-Hydroxy-phenyl)-4-morpholin-4-yl-thieno[3,2-d]pyrimidin-6-ylmethyl]-piperazine-1-carboxylic acid ethylamide;
N-{1-[2-(3-Hydroxy-phenyl)-4-morpholin-4-yl-thieno[3,2-d]pyrimidin-6-ylmethyl]-piperidin-4-yl}-methanesulfonamide;
1-{4-[2-(3-Hydroxy-phenyl)-4-morpholin-4-yl-thieno[3,2-d]pyrimidin-6-ylmethyl]-piperazin-1-yl}-2-methoxy-ethanone;
N-{1-[2-(3-Hydroxy-phenyl)-4-morpholin-4-yl-thieno[3,2-d]pyrimidin-6-ylmethyl]-piperidin-4-yl}-acetamide;
4-[2-(3-Hydroxy-phenyl)-4-morpholin-4-yl-thieno[3,2-d]pyrimidin-6-ylmethyl]-piperazine-1-carboxylic acid dimethylamide;
1-[2-(3-Hydroxy-phenyl)-4-morpholin-4-yl-thieno[3,2-d]pyrimidin-6-ylmethyl]-piperidin-4-ol;
3-[6-(1,1-Dioxo-thiomorpholin-4-ylmethyl)-4-morpholin-4-yl-thieno[3,2-d]pyrimidin-2-yl]-phenol
4-[2-(3-Hydroxy-phenyl)-4-morpholin-4-yl-thieno[3,2-d]pyrimidin-6-ylmethyl]-piperazine-1-sulfonic acid dimethylamide;
3-(6-{4-[(2-Methoxy-ethyl)-methyl-amino]-piperidin-1-ylmethyl}-4-morpholin-4-yl-thieno[3,2-d]pyrimidin-2-yl)-phenol;
1-[2-(3-Hydroxy-phenyl)-4-morpholin-4-yl-thieno[3,2-d]pyrimidin-6-ylmethyl]-pyrrolidin-3-ol;
(R,S)-3-[6-(2-Dimethylaminomethyl-pyrrolidin-1-ylmethyl)-4-morpholin-4-yl-thieno[3,2-d]pyrimidin-2-yl]-phenol;
(R,S)-3-(6-{[Methyl-(1-methyl-pyrrolidin-2-ylmethyl)-amino]-methyl}-4-morpholin-4-yl-thieno[3,2-d]pyrimidin-2-yl)-phenol;
1-[2-(3-Hydroxy-phenyl)-4-morpholin-4-yl-thieno[3,2-d]pyrimidin-6-ylmethyl]-piperidine-4-carboxylic acid amide;
2-{4-[2-(3-Hydroxy-phenyl)-4-morpholin-4-yl-thieno[3,2-d]pyrimidin-6-ylmethyl]-piperazin-1-yl}-N,N-dimethyl-acetamide;
3-(6-{[Methyl-(1-methyl-pyrrolidin-3-yl)-amino]-methyl}-4-morpholin-4-yl-thieno[3,2-d]pyrimidin-2-yl)-phenol;
2-Dimethylamino-1-{4-[2-(3-hydroxy-phenyl)-4-morpholin-4-yl-thieno[3,2-d]pyrimidin-6-ylmethyl]-piperazin-1-yl}-ethanone;
3-[6-((3R,5S)-3,5-Dimethyl-piperazin-1-ylmethyl)-4-morpholin-4-yl-thieno[3,2-d]pyrimidin-2-yl]-phenol;
3-[6-((3R,5S)-4-Methanesulfonyl-3,5-dimethyl-piperazin-1-ylmethyl)-4-morpholin-4-yl-thieno[3,2-d]pyrimidin-2-yl]-phenol;
1-{(2R,6S)-4-[2-(3-Hydroxy-phenyl)-4-morpholin-4-yl-thieno[3,2-d]pyrimidin-6-ylmethyl]-2,6-dimethyl-piperazin-1-yl}-ethanone;

3-{6-[4-(3-Dimethylamino-propane-1-sulfonyl)-piperazin-1-ylmethyl]-4-morpholin-4-yl-thieno[3,2-d]pyrimidin-2-yl}-phenol;

3-[6-(4-Methoxy-piperidin-1-ylmethyl)-4-morpholin-4-yl-thieno[3,2-d]pyrimidin-2-yl]-phenol;

3-{4-Morpholin-4-yl-6-[4-(3-morpholin-4-yl-propane-1-sulfonyl)-piperazin-1-ylmethyl]-thieno[3,2-d]pyrimidin-2-yl}-phenol;

{4-[2-(3-Hydroxy-phenyl)-4-morpholin-4-yl-thieno[3,2-d]pyrimidin-6-ylmethyl]-piperazin-1-yl}-morpholin-4-yl-methanone;

4-[2-(3-Hydroxy-phenyl)-4-morpholin-4-yl-thieno[3,2-d]pyrimidin-6-ylmethyl]-piperazine-1-carboxylic acid (2-methoxy-ethyl)-methyl-amide;

1-{3-[6-(4-Methyl-piperazin-1-ylmethyl)-4-morpholin-4-yl-thieno[3,2-d]pyrimidin-2-yl]-phenyl}-ethanol;

3-[6-(4-Methyl-piperazin-1-ylmethyl)-4-morpholin-4-yl-thieno[3,2-d]pyrimidin-2-yl]-phenyl}-methanol;

2-Chloro-5-[6-(4-methyl-piperazin-1-ylmethyl)-4-morpholin-4-yl-thieno[3,2-d]pyrimidin-2-yl]-phenol;

2,3-Difluoro-5-[6-(4-methyl-piperazin-1-ylmethyl)-4-morpholin-4-yl-thieno[3,2-d]pyrimidin-2-yl]-phenol;

4-Fluoro-3-[6-(4-methyl-piperazin-1-ylmethyl)-4-morpholin-4-yl-thieno[3,2-d]pyrimidin-2-yl]-phenol;

2-(1H-Indazol-6-yl)-6-(4-methyl-piperazin-1-ylmethyl)-4-morpholin-4-yl-thieno[3,2-d]pyrimidin-2-yl]-phenol; and 6-(4-Methyl-piperazin-1-ylmethyl)-4-morpholin-4-yl-2-(1H-pyrazol-4-yl)-thieno[3,2-d]pyrimidine;

and the pharmaceutically acceptable salts thereof.

The compounds of formula (I) may exist in the form of geometrical isomers or tautomers depending on the kinds of substituent groups, and these isomers in separated forms or mixtures thereof may be used in the present invention. Where the compounds have asymmetric carbon atoms, optical isomer forms may exist based on such carbon atoms. All of the mixtures and the isolated forms of these optical isomers may be used in the present invention.

A suitable synthetic strategy for producing compounds of formula (I) in which m is 1 employs the precursor carboxaldehyde of formula (II):

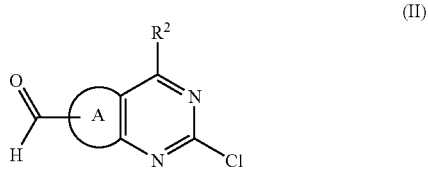

(II)

wherein A and $R^2$ are as defined above. Starting from this precursor the synthesis comprises performing, in either order, a palladium-mediated (Suzuki-type) cross-coupling reaction and a reductive amination. The present invention therefore further provides a process for producing a compound of formula (I) as defined above in which m is 1, which process comprises:

(a) treating a compound of formula (II):

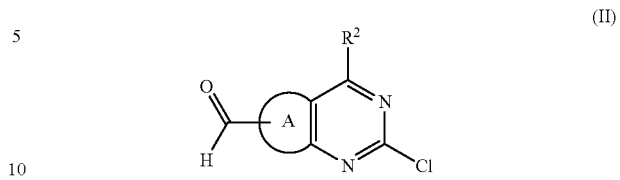

(II)

wherein A and $R^2$ are as defined above, with a boronic acid or ester thereof of formula $R^3B(OR^{15})_2$, in which $R^3$ is as defined above and each $R^{15}$ is H or $C_1$-$C_6$ alkyl or the two groups $OR^{15}$ form, together with the boron atom to which they are attached, a pinacolato boronate ester group, in the presence of a Pd catalyst; and treating the resulting compound of formula (III):

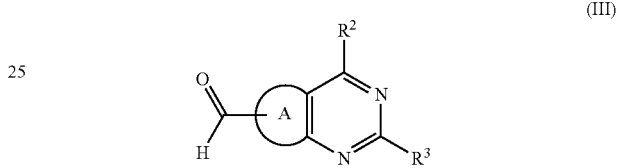

(III)

wherein A, $R^2$ and $R^3$ are as defined above, with an amine of formula $NHR^4R^5$ in which $R^4$ and $R^5$ are as defined above, in the presence of a suitable reducing agent; or (b) treating a compound of formula (II) as defined above with an amine of formula $NHR^4R^5$ wherein $R^4$ and $R^5$ are as defined above, in the presence of a suitable reducing agent; and treating the resulting compound of formula (IV):

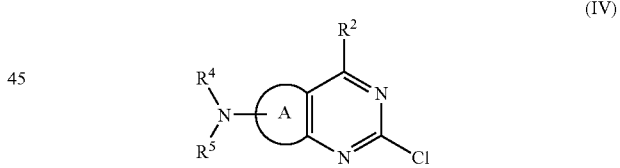

(IV)

wherein A, $R^2$, $R^4$ and $R^5$ are as defined above, with a boronic acid or ester thereof of formula $R^3B(OR^{15})_2$, in which $R^3$ is as defined above and each $R^{15}$ is H or $C_1$-$C_6$ alkyl or the two groups $OR^{15}$ form, together with the boron atom to which they are attached, a pinacolato boronate ester group, in the presence of a Pd catalyst.

Both the amination step and the Pd-mediated cross-coupling step take place under conventional conditions. The palladium catalyst may be any that is typically used for Suzuki-type cross-couplings, such as $PdCl_2(PPh_3)_2$. The reducing agent is typically a borohydride, for instance $NaBH(OAc)_3$, $NaBH_4$ or $NaCNBH_4$, in particular $NaBH(OAc)_3$.

The invention further provides a process for producing a compound of formula (I) in which m is 1 and $R^3$ is a 3- or 4-hydroxyphenyl group, which process comprises:

(a) treating a compound of formula (V):

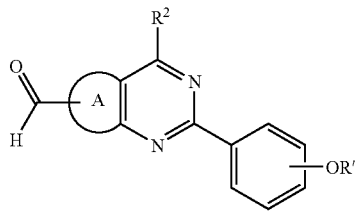

wherein OR' is bonded at position 3 or 4 of the phenyl ring to which it is attached, R' is a hydroxy protecting group and A and $R^2$ are as defined above, with an amine of formula $NHR^4R^5$ wherein $R^4$ and $R^5$ are as defined above, in the presence of a suitable reducing agent; and (b) removing the hydroxy protecting group.

The reducing agent is typically a borohydride, for instance as specified above.

Examples of hydroxy protecting groups are known in the art, for instance as described in "Protective Groups for Organic Chemistry", Third Edition, T. W. Greene and P. G. M. Wuts, John Wiley & Sons, 1999. For instance, a hydroxy group can be protected as an acetal, a substituted acetal, an ester, a xanthate, an ether or a silyl ether. The acetal is preferably tetrahydropyran. The silyl ether is preferably trimethylsilyl ether, t-butyl dimethylsilyl ether, triiso-propylsilyl ether or t-butyldiphenyl-silyl ether. These protecting groups are removed by conventional techniques.

A compound of formula (V) as defined above may be produced by a process which comprises treating a compound of formula (VI):

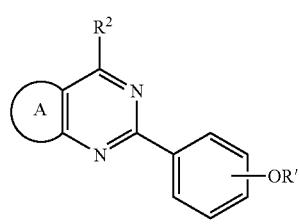

wherein A, $R^2$ and R' are as defined above, with a lithiating agent followed by N,N'-dimethylformamide (DMF). The reaction is typically conducted by adding a solution of the lithiating agent in a non-polar organic solvent, for instance a hydrocarbon solvent such as hexane, to a suspension of the compound of formula (VI) in an organic solvent such as tetrahydrofuran (THF). If THF is used the addition takes place at a low temperature, of about −78° C. The lithiating agent is typically an alkyllithium, for instance n-butyllithium.

A compound of formula (VI) as defined above may be produced by a process which comprises treating a compound of formula (VII):

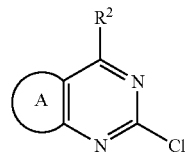

wherein A and $R^2$ are as defined above, with a boronic acid of formula (VIII):

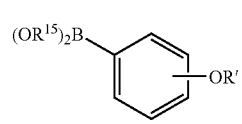

wherein R' and $R^{15}$ are as defined above, in the presence of a palladium catalyst. The reaction is conducted under conventional conditions for a Suzuki-type cross-coupling reaction, for instance as described above.

A compound of formula (II) as defined above wherein $R^2$ is $-NR^6R^7$ may be prepared by a process which comprises treating a compound of formula (IX):

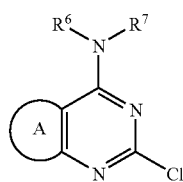

wherein A, $R^6$ and $R^7$ are as defined above, with a lithiating agent followed by N,N'-dimethylformamide (DMF). The reaction is typically carried out as described above for the production of a compound of formula (V).

A compound of formula (IX) as defined above may be produced by a process which comprises treating a compound of formula (X):

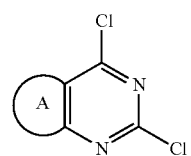

with an amine of formula $NHR^6R^7$, wherein $R^6$ and $R^7$ are as defined above, in an organic solvent. The solvent is typically an alcohol, such as methanol. The reaction is generally conducted at room temperature.

A compound of formula (X) may be prepared by the process described in Reference Example 1 for the preparation of 2,4-dichloro-thieno[3,2-d]pyrimidine, or by analogy with such a process.

A compound of formula (II) as defined above wherein $R^2$ is of formula

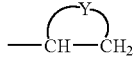

may be prepared by a process which comprises submitting a compound of formula (XI):

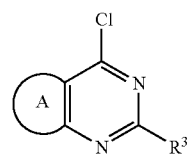

wherein A and $R^3$ are as defined above, to palladium-mediated cross-coupling with a compound of formula (XII):

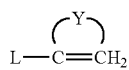

wherein L is H or a group selected from halo, $-OSO_2CF_3$, $-B(OR)_2$, $-Sn(R)_3$ and $-Si(R)_3$ wherein R is H or alkyl as defined above, followed by reduction, to yield a compound of the following formula (XIII):

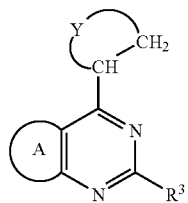

wherein A, $R^3$ and Y are as defined above.

The compound of formula (XIII) may be converted to the corresponding carboxaldehyde by treatment with a lithiating agent followed by N,N'-dimethylformamide (DMF), for instance under the conditions described above for the conversion of a compound of formula (VI) to a compound of formula (V). The lithiating agent is typically as defined above. The resulting carboxaldehyde may then be converted into a desired final compound of formula (I) as defined above, in which m is 1, by treatment with an amine of formula $NHR^4R^5$ in which $R^4$ and $R^5$ are as defined above, in the presence of a suitable reducing agent, for instance a borohydride as specified above, in particular $NaBH(OAc)_3$.

A compound of formula (I) as defined above in which m is 0 may be prepared by a Buchwald-type palladium-mediated nitrogen insertion reaction. Such a process may comprise treating a compound of formula (XIV):

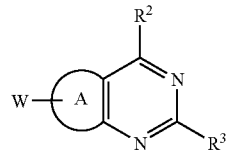

wherein A, $R^2$ and $R^3$ are as defined above and W is a halo group selected from Br and I, with an amine of formula $NHR^4R^5$ in which $R^4$ and $R^5$ are as defined above, in the presence of a palladium catalyst.

A compound of formula (XIV) may be produced by treating a compound of formula (XV):

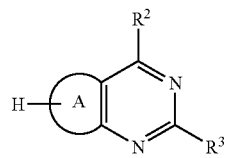

wherein A, $R^2$ and $R^3$ are as defined above, with a lithiating agent and a halogen selected from bromine and iodine. The lithiating agent is typically an alkyllithium, for instance butyllithium. The halogen is typically iodine, which gives rise to a compound of formula (XIV) in which W is I.

A compound of formula (I) as defined above in which m is 0 may also be prepared by an SNAr displacement reaction, for instance under the conditions described by D. Prim and G. Kirsch in Tetrahedron 55 (21), 6511-6526, 1999. Such a process comprises treating a compound of formula (XIV) as defined above in which W is Br with an amine of formula $NHR^4R^5$ in which $R^4$ and $R^5$ are as defined above in $H_2O$ under reflux for 12 hours.

A compound of formula (I) as defined above in which m is 0 may alternatively be prepared by treating a compound of formula (XIV) as defined above in which W is I with an amine of formula $NHR^4R^5$ in which $R^4$ and $R^5$ are as defined above in 1,4-dioxane in the presence of CuI/En and $K_3PO_4$. The reaction is conducted at about 110° C. for 24 hours. This procedure is described by Kang S-K et al in Synlett, (3), 427-430, 2002.

A fused pyrimidine of formula (I) may be converted into a pharmaceutically acceptable salt, and a salts may be converted into the free compound, by conventional methods. Examples of pharmaceutically acceptable salts include acid addition salts with inorganic acids such as hydrochloric acid, hydrobromic acid, hydroiodic acid, sulphuric acid, nitric acid and phosphoric acid; and organic acids such as formic acid, acetic acid, trifluoroacetic acid, propionic acid, oxalic acid, malonic acid, succinic acid, fumaric acid, maleic acid, lactic acid, malic acid, tartaric acid, citric acid, methanesulfonic acid, ethanesulfonic acid, aspartic acid and glutamic acid. In the case of compounds of the invention bearing a free carboxy substituent, the salts include the salts of alkali and alkaline earth metals and ammonium, for instance the salts of sodium, potassium, magnesium, calcium and ammonium. The latter are prepared by treating the free fused pyrimidine of formula (I), or an acid addition salt thereof, with the corresponding metal base or ammonia. The compounds of formula (I) and their salts may exist as hydrates or solvates.

Compound of the present invention have been found in biological tests to be inhibitors of PI3 kinase. The compounds are selective for class Ia PI3 kinases over class Ib and typically exhibit at least a 20-fold selectivity for class Ia over class Ib PI3 kinases. In particular, the compounds are selective for the p110α isoform.

A compound of the present invention may thus be used as an inhibitor of PI3 kinase, in particular of a class Ia PI3 kinase. Accordingly, a compound of the present invention can be used to treat a disease or disorder arising from abnormal cell growth, function or behaviour associated with PI3 kinase. Examples of such diseases and disorders are discussed by Drees et al in Expert Opin. Ther. Patents (2004) 14(5):703-732. These include cancer, immune disorders, cardiovascular disease, viral infection, inflammation, metabolism/endocrine disorders and neurological disorders. Examples of metabolism/endocrine disorders include diabetes and obesity. Examples of cancers which the present compounds can be used to treat include leukaemia, brain tumours, renal cancer, gastric cancer and cancer of the skin, bladder, breast, uterus, lung, colon, prostate, ovary and pancreas.

A human or animal patient suffering from an immune disorder, cancer, cardiovascular disease, viral infection, inflammation, a metabolism/endocrine disorder or a neurological disorders may thus be treated by a method comprising the administration thereto of a compound of the present invention as defined above. The condition of the patient may thereby be improved or ameliorated.

In addition to possessing biochemical potency the compounds of the invention exhibit physicochemical and pharmacokinetic properties which make them particularly well adapted for drug use. This is shown for instance in the results of the biological assays described in Example 11, which follows. In particular the compounds possess high aqueous solubility at physiological pH; many have a solubility of at least 40 μM and a significant number have a solubility of greater than 100 μM. High solubility at physiological pH is desirable since it promotes bioavailability. The compounds also possess high metabolic stability, as shown in particular by the hepatocyte clearance assay described in Example 11 in which most of the tested compounds were shown to have low hepatocyte clearance. Low hepatocyte clearance correlates with a low rate of liver metabolism. It can therefore be seen that the compounds of the present invention possess improved physicochemical and pharmacokinetic properties whilst retaining biochemical potency as inhibitors of PI3 kinase.

A compound of the present invention can be administered in a variety of dosage forms, for example orally such as in the form of tablets, capsules, sugar- or film-coated tablets, liquid solutions or suspensions or parenterally, for example intramuscularly, intravenously or subcutaneously. The compound may therefore be given by injection or infusion.

The dosage depends on a variety of factors including the age, weight and condition of the patient and the route of administration. Daily dosages can vary within wide limits and will be adjusted to the individual requirements in each particular case. Typically, however, the dosage adopted for each route of administration when a compound is administered alone to adult humans is 0.0001 to 50 mg/kg, most commonly in the range of 0.001 to 10 mg/kg, body weight, for instance 0.01 to 1 mg/kg. Such a dosage may be given, for example, from 1 to 5 times daily. For intravenous injection a suitable daily dose is from 0.0001 to 1 mg/kg body weight, preferably from 0.0001 to 0.1 mg/kg body weight. A daily dosage can be administered as a single dosage or according to a divided dose schedule.

A compound is formulated for use as a pharmaceutical or veterinary composition also comprising a pharmaceutically or veterinarily acceptable carrier or diluent. The compositions are typically prepared following conventional methods and are administered in a pharmaceutically or veterinarily suitable form. The compound may be administered in any conventional form, for instance as follows:

A) Orally, for example, as tablets, coated tablets, dragees, troches, lozenges, aqueous or oily suspensions, liquid solutions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of sweetening agents, flavouring agents, colouring agents and preserving agents in order to provide pharmaceutically elegant and palatable preparations.

Tablets contain the active ingredient in admixture with non-toxic pharmaceutically acceptable excipients which are suitable for the manufacture of tablets. These excipients may be for example, inert diluents, such as calcium carbonate, sodium carbonate, lactose, dextrose, saccharose, cellulose, corn starch, potato starch, calcium phosphate or sodium phosphate; granulating and disintegrating agents, for example, maize starch, alginic acid, alginates or sodium starch glycolate; binding agents, for example starch, gelatin or acacia; lubricating agents, for example silica, magnesium or calcium stearate, stearic acid or talc; effervescing mixtures; dyestuffs, sweeteners, wetting agents such as lecithin, polysorbates or lauryl sulphate. The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed. Such preparations may be manufactured in a known manner, for example by means of mixing, granulating, tableting, sugar coating or film coating processes.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is present as such, or mixed with water or an oil medium, for example, peanut oil, liquid paraffin, or olive oil.

Aqueous suspensions contain the active materials in admixture with excipients suitable for the manufacture of aqueous suspensions. Such excipients are suspending agents, for example, sodium carboxymethylcellulose, methylcellulose, hydroxypropylmethyl-cellulose, sodium alginate, polyvinylpyrrolidone gum tragacanth and gum acacia; dispersing or wetting agents may be naturally-occurring phosphatides, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides for example polyoxyethylene sorbitan monooleate.

The said aqueous suspensions may also contain one or more preservatives, for example, ethyl or n-propyl p-hydroxybenzoate, one or more colouring agents, such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol.

Sweetening agents, such as those set forth above, and flavouring agents may be added to provide a palatable oral preparation. These compositions may be preserved by this addition of an antioxidant such as ascorbic acid. Dispersible powders and granules suitable for preparation of an aqueous suspension by the addition of water provide the active ingredient in admixture with a dispersing or wetting agent, a suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally occurring phosphatides, for example soy bean lecithin, and esters or partial esters derived from fatty acids an hexitol anhydrides, for example sorbitan mono-oleate, and condensation products of the said partial esters with ethylene oxide, for example polyoxyethylene sorbitan monooleate. The emulsion may also contain sweetening and flavouring agents. Syrups and elixirs may be formulated with sweetening agents, for example glycerol, sorbitol or sucrose. In particular a syrup for diabetic patients can contain as carriers only products, for example sorbitol, which do not metabolise to glucose or which only metabolise a very small amount to glucose.

Such formulations may also contain a demulcent, a preservative and flavouring and coloring agents;

B) Parenterally, either subcutaneously, or intravenously, or intramuscularly, or intrasternally, or by infusion techniques, in the form of sterile injectable aqueous or oleaginous suspensions. This suspension may be formulated according to the known art using those suitable dispersing of wetting agents and suspending agents which have been mentioned above. The sterile injectable preparation may also be a sterile injectable solution or suspension in a non-toxic paternally-acceptable diluent or solvent, for example as a solution in 1,3-butane diol.

Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition fatty acids such as oleic acid find use in the preparation of injectables;

C) By inhalation, in the form of aerosols or solutions for nebulizers;

D) Rectally, in the form of suppositories prepared by mixing the drug with a suitable non-irritating excipient which is solid at ordinary temperature but liquid at the rectal temperature and will therefore melt in the rectum to release the drug. Such materials are cocoa butter and poly-ethylene glycols;

E) Topically, in the form of creams, ointments, jellies, collyriums, solutions or suspesions.

The invention will be further described in the Examples which follow:

Example 1

3-[6-(4-Methyl-piperazin-1-ylmethyl)-4-morpholin-4-yl-thieno[3,2-d]pyrimidin-2-yl]-phenol (9)

The synthetic route to compound 9 is shown in the following scheme.

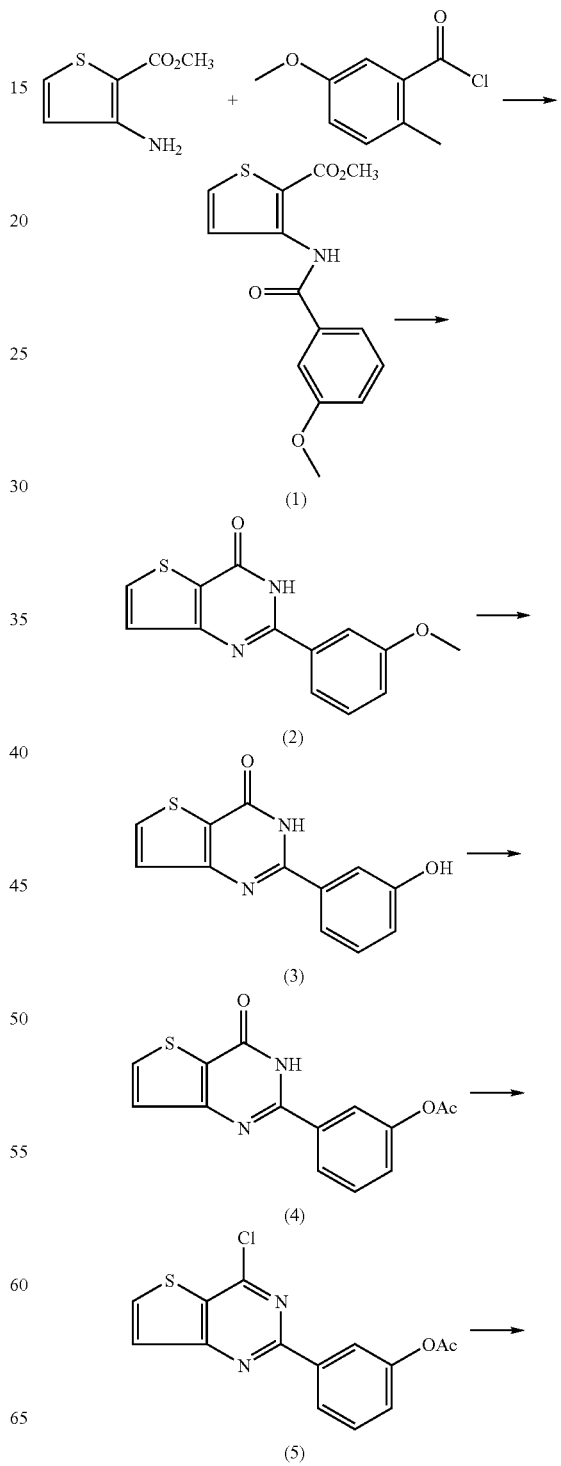

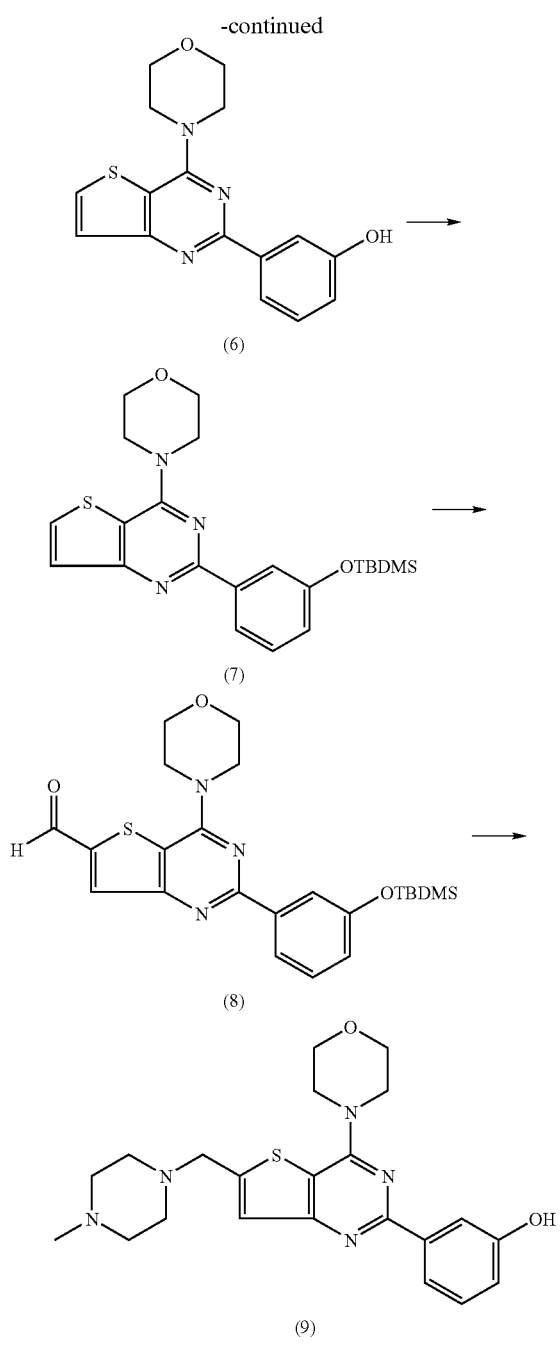

additional quantity of product precipitated from the water-acetonitrile solution; this was collected in the same fashion. (Total yield: 14.08 g, 95%).
$^1$H NMR (400 MHz, CDCl$_3$) 3.89 (s, 3H), 3.93 (s, 3H), 7.12 (dd, 1H, J=2.2, 8.4), 7.42 (t, 1H, J=7.9), 7.54 (d, 1H, J=5.5), 7.58 (m, 1H), 8.29 (d, 1H, J=5.5), 11.17 (brs, 1H).

Preparation of 2-(3-Methoxy-phenyl)-3H-thieno[3,2-d]pyrimidin-4-one (2)

Ammoniacal methanol was prepared by bubbling ammonia (30-32 g) through methanol (190 mL) cooled in ice-water. To the solution was added 3-(3-methoxy-benzoylamino)-thiophene-2-carboxylic acid methyl ester (18.00 g, 61.8 mmol) and the mixture heated at 90° C. for 44 hours in a steel bomb at 50 psi. The solvent was then removed in vacuo and isopropanol (300 mL) added followed by 2M aqueous sodium hydroxide (4.0 eq., 124 mL). The solution was heated under reflux for 15 hours and then cooled in ice-water. The mixture was acidified to pH 1 by the addition of 4 M hydrochloric acid and the white precipitate collected by filtration, washed with water and dried to give compound 2 (15.20 g, 95%).
$^1$H NMR (400 MHz, d$_6$-DMSO) 3.86 (s, 3H), 7.14 (dd, 1H, J=2.2, 8.2), 7.45 (m, 2H), 7.70 (s, 1H), 7.74 (d, 1H, J=7.8), 8.22 (d, 1H, J=5.2), 12.70 (brs, 1H), Preparation of 2-(3-Hydroxy-phenyl)-3H-thieno[3,2-d]pyrimidin-4-one (3)

To a suspension of 2-(3-methoxy-phenyl)-3H-thieno[3,2-d]pyrimidin-4-one (30.31 g, 0.12 mol) in acetic acid (170 mL) was added 48% aqueous hydrogen bromide (170 mL) and the mixture heated under reflux for 48 hours. The mixture was then cooled in ice-water and diluted with water (200 mL). The grey solid was collected by filtration, washed with water and dried to give compound 3 (28.58 g, 100%).
$^1$H NMR (400 MHz, d$_6$-DMSO) 6.87 (m, 1H), 7.23 (t, 1H, J=8.0), 7.36 (d, 1H, J=5.2), 7.45 (m, 2H), 8.13 (d, 1H, J=5.2), 9.67 (brs, 1H), 12.52 (brs, 1H).

Preparation of Acetic acid 3-(4-oxo-3,4-dihydro-thieno[3,2-d]pyrimidin-2-yl)-phenyl ester (4)

A mixture of 2-(3-hydroxy-phenyl)-3H-thieno[3,2-d]pyrimidin-4-one (28.58 g, 0.12 mol) and sodium acetate (1.1 eq., 0.13 mol, 10.56 g) in acetic anhydride (280 mL) was heated under reflux for 1.5 hours. The mixture was then cooled in ice-water and the grey solid collected by filtration, washed with water and dried to yield compound 4 (27.69 g, 82%).
$^1$H NMR (400 MHz, d$_6$-DMSO) 2.32 (s, 3H), 7.36 (dd, 1H, J=2.0, 8.0), 7.47 (d, 1H, J=5.2), 7.59 (d, 1H, J=8.0), 7.93 (s, 1H), 8.04 (d, 1H, J=7.9), 8.22 (d, 1H, J=5.2), 12.75 (brs, 1H).

Preparation of 3-(4-Chloro-thieno[3,2-d]pyrimidin-2-yl)-phenol and Acetic acid 3-(4-chloro-thieno[3,2-d]pyrimidin-2-yl)-phenyl ester (5)

To the pyrimidone (26.65 g, 93.1 mmol) was added phosphorus oxychloride (130 mL, 15 eq.) and the dark mixture heated under reflux for 3 hours. Most of the phosphorus oxychloride was removed by distillation at reduced pressure and the residue transferred to a conical flask and cooled in ice-water. The mixture was quenched by the addition of ice-water and then saturated aqueous sodium hydrogen carbonate added (600 mL). The solid was collected by filtration and re-suspended in aqueous sodium hydrogen carbonate, such Preparation of 3-(3-Methoxy-benzoylamino)-thiophene-2-carboxylic acid methyl ester (1)

To a solution of methyl-3-amino-2-thiophenecarboxylate (8.00 g, 50.9 mmol) in acetonitrile (100 mL) was added potassium carbonate (1.1 eq., 56.0 mmol, 7.73 g) followed by m-anisoyl chloride (1.05 eq., 53.4 mmol, 7.51 mL) and the mixture heated under reflux for 1 hour. A white precipitate forms. The mixture was cooled in ice-water, diluted with water (100 mL) and the white solid collected by filtration and dried to yield compound 1 (12.78 g). Upon standing, an that the pH was greater than 7. The solid was collected by filtration, washed thoroughly with water and dried to yield a mixture of the chloropyrimidines 5 in the ratio 1.5:1 (24.0 g).

3-(4-Chloro-thieno[3,2-d]pyrimidin-2-yl)-phenol: $^1$H NMR (400 MHz, d$_6$-DMSO) 6.94 (dd, 1H, J=1.6, 7.6). 7.35 (t, 1H, J=7.8), 7.76 (d, 1H, J=5.4), 7.87 (m, 2H), 8.58 (d, 1H, J=5.4), 9.67 (brs, 1H).

Acetic acid 3-(4-chloro-thieno[3,2-d]pyrimidin-2-yl)-phenyl ester: $^1$H NMR (400 MHz, CDCl$_3$) 2.35 (s, 3H), 7.24 (m, 1H), 7.52 (t, 1H, J=8.0), 7.61 (d, 1H, J=5.4), 8.04 (d, 1H, J=5.4), 8.28 (t, 1H, J=2.0), 8.43 (dd, 1H, J=1.7, 7.9).

Preparation of 3-(4-Morpholin-4-yl-thieno[3,2-d]pyrimidin-2-yl)-phenol (6)

To a mixture of the chloropyrimidines (24.0 g) in n-butanol, (220 mL) was added morpholine (3.5 eq., 0.33 mol, 28.3 mL) and the mixture heated at 100° C. for 2 hours. The solvent was removed in vacuo and water added to the residue. The pale brown solid was collected by filtration and dried in a vacuum oven to give compound 6 as a pale brown solid (20.3 g, 70%).

$^1$H NMR (400 MHz, d$_6$-DMSO) 3.81 (t, 4H, J=4.8), 4.01 (t, 4H, J=4.8), 6.86 (m, 1H), 7.27 (t, 1H, J=8.0), 7.51 (d, 1H, J=5.6), 7.86 (m, 2H), 8.25 (d, 1H, J=5.6), 9.46 (brs, 1H).

Preparation of 2-[3-(tert-Butyl-dimethyl-silanyloxy)-phenyl]-4-morpholin-4-yl-thieno[3,2-d]pyrimidine (7)

A mixture of 3-(4-morpholin-4-yl-thieno[3,2-d]pyrimidin-2-yl)-phenol (17.28 g, 55.1 mmol), imidazole (1.7 eq., 93.7 mmol, 6.38 g) and tert-butyldimethylsilyl chloride (1.5 eq., 82.7 mmol. 12.47 g) in DMF (45 mL) was heated at 50° C. for 5 hours. The reaction mixture was then cooled and partitioned between water (400 mL) and ether (3×400 mL). The combined organic layers were washed sequentially with saturated aqueous sodium hydrogen carbonate (300 mL), brine (300 mL), separated and dried (MgSO$_4$). The crude product was evaporated onto silica and purified by chromatography (5%→20% ethyl acetate-petrol) to yield compound 7 as a white solid (19.60 g, 83%).

$^1$H NMR (400 MHz, CDCl$_3$) 0.15 (s, 6H), 0.92 (s, 9H), 3.80 (t, 4H, J=4.8), 3.98 (t, 4H, J=4.8), 6.83 (td, 1H, J=1.5, 8.3), 7.22 (t, 1H, J=7.9), 7.41 (d, 1H, J=5.5), 7.64 (d, 1H, J=5.5), 7.84 (t, 1H, J=2.0), 7.95 (d, 1H, J=7.8).

Preparation of 4-Morpholin-4-yl-2-[3-(1,1,2,2-tetramethyl-propylsilanyloxy)-phenyl]-thieno[3,2-d]pyrimidine-6-carbaldehyde (8)

To a solution of 4-morpholin-4-yl-2-[3-(1,1,2,2-tetramethyl-propylsilanyloxy)-phenyl]-thieno[3,2-d]pyrimidine (2.26 g, 5.29 mmol) in dry THF (40 mL) cooled to −78° C. was added nBuLi (2.5 M solution in hexanes, 2.75 mL, 1.3 eq.). After stirring for 20 minutes, dry N,N-dimethylformamide (617 μL, 1.5 eq.) was added, and the reaction mixture was stirred for 20 minutes at −78° C. and then warmed slowly to room temperature. After a further 30 minutes at room temperature the reaction mixture was quenched with ice/brine and then extracted exhaustively with chloroform. The combined organic extracts were dried (MgSO$_4$) and the solvent removed in vacuo to yield compound 8 as a yellow solid (2.38 g, 99%).

Preparation of 3-[6-(4-Methyl-piperazin-1-ylmethyl)-4-morpholin-4-yl-thieno[3,2-d]pyrimidin-2-yl]-phenol (9)

A mixture of 4-morpholin-4-yl-2-[3-(1,1,2,2-tetramethyl-propylsilanyloxy)-phenyl]-thieno[3,2-d]pyrimidine-6-carbaldehyde (6.67 g, 14.66 mmol), N-methylpiperazine (2.11 mL, 1.3 equivalents) and acetic acid (838 μL, 1.0 eq.) was stirred in 1,2-dichloroethane (70 mL) at room temperature. To this was added sodium triacetoxyborohydride (3.42 g, 1.1 equivalents) and the reaction mixture was stirred for 3 days. The reaction mixture was then quenched with aqueous sodium bicarbonate solution, extracted exhaustively with chloroform, dried (MgSO$_4$), and the solvent removed in vacuo to yield a yellow oil. This was purified using flash chromatography (silica, ethyl acetate to ethyl acetate/methanol) to yield 6-(4-methyl-piperazin-1-ylmethyl)-4-morpholin-4-yl-2-[3-(1,1,2,2-tetramethyl-propylsilanyloxy)-phenyl]-thieno[3,2-d]pyrimidine (6.95 g, 88%).

To a solution of 6-(4-methyl-piperazin-1-ylmethyl)-4-morpholin-4-yl-2-[3-(1,1,2,2-tetramethyl-propylsilanyloxy)-phenyl]-thieno[3,2-d]pyrimidine (6.95 g, 12.89 mmol) in THF (100 mL) cooled to 0° C. was added a 1.0 M solution of tetrabutyl ammonium fluoride in THF (14.2 mL, 1.1 eq.). After 30 minutes the solvent was removed in vacuo and the residue was purified using flash chromatography (silica, 8% methanol in dichloromethane) and then triturated using ethyl acetate/methanol to yield the title compound as a white solid (4.62 g, 85%).

$^1$H NMR (400 MHz, CDCl$_3$) 2.27 (s, 3H, CH$_3$), 2.49 (br s, 8H, 4×CH$_2$), 3.79 (s, 2H, CH$_2$), 3.82-3.84 (m, 4H, 2×CH$_2$), 4.0-4.03 (m, 4H, 2×CH$_2$), 6.88-6.91 (m, H, ArH), 7.24-7.28 (m, 2H, 2×ArH part under CDCl$_3$), 7.69-7.70 (m, H, ArH), 7.81 (d, H, ArH, J=7.8 Hz); MS (ESI$^+$) 426 (MH$^+$).

Example 2

Further Compounds of the Invention

The following compounds of the invention were prepared by analogy with the procedure described in Example 1, using the appropriate amine. The amines are commercially available compounds unless stated otherwise. Characterising data are also given for the compounds of the invention.

10: 3-(4-Morpholin-4-yl-6-morpholin-4-ylmethyl-thieno[3,2-d]pyrimidin-2-yl)-phenol was prepared using morpholine.

$^1$H NMR (400 MHz, CDCl$_3$) 2.55 (m, 4H), 3.75-3.79 (m, 4H), 3.82 (s, 2H), 3.93-3.96 (m, 4H), 4.04-4.00 (m, 4H), 6.95 (d, 2H), 7.36-7.30 (m, 2H), 7.99-7.91 (m, 2H); MS (ESI$^+$) 413 (MH$^+$).

11: 3-(4-Morpholin-4-yl-6-pyrrolidin-1-ylmethyl-thieno[3,2-d]pyrimidin-2-yl)-phenol was prepared using pyrrolidine.

$^1$H NMR (400 MHz, CDCl$_3$) 1.87-1.90 (m, 4H), 2.65-2.70 (m, 4H), 3.82-3.88 (m, 4H), 3.99-4.03 (m, 6H), 6.95 (d, 2H), 7.30-7.36 (m, 2H), 7.80 (s, 1H), 7.99 (d, 1H); MS (ESI$^+$) 397 (MH$^+$).

12: 3-[6-(6,7-Dimethoxy-3,4-dihydro-1H-isoquinolin-2-ylmethyl)-4-morpholin-4-yl-thieno[3,2-d]pyrimidin-2-yl]-phenol was prepared using 6,7-dimethoxy-1,2,3,4-tetrahydroisoquinoline.

$^1$H NMR (400 MHz, CDCl$_3$) 2.86-2.88 (m, 4H), 3.70 (s, 2H), 3.83 (s, 3H), 3.85-3.89 (m, 7H), 3.97-4.02 (m, 6H), 5.11 (br s, 1H), 6.51 (s, 1H), 6.60 (s, 1H), 6.95 (d, 1H), 7.35-7.30 (m, 2H), 7.92 (s, 1H), 8.01 (d, 1H); MS (ESI$^+$) 519 (MH$^+$).

13: 3-(6-[1,4']Bipiperidinyl-1'-ylmethyl-4-morpholin-4-yl-thieno[3,2-d]pyrimidin-2-yl)-phenol was prepared using 4-piperidinopiperidine.

¹H NMR (400 MHz, CDCl₃) 1.42-1.48 (m, 2H), 1.54-1.68 (m, 6H), 1.82-1.84 (m, 2H), 2.01-2.05 (m, 2H), 2.28-2.30 (m, 1H), 2.48-2.52 (m, 4H), 2.97-2.99 (m, 2H), 3.79 (s, 2H), 3.85-3.89 (m, 4H), 3.99-4.02 (m, 4H), 6.90 (d, 1H), 7.29-7.38 (m, 2H), 7.90 (s, 1H), 7.99 (d, 1H); MS (ESI⁺) 494 (MH⁺).

14: 3-[4-Morpholin-4-yl-6-(4-pyrimidin-2-yl-piperazin-1-ylmethyl)-thieno[3,2-d]pyrimidin-2-yl]-phenol was prepared using 1-(2-pyrimidyl)piperazine.

¹H NMR (400 MHz, CDCl₃) 2.58-2.62 (m, 4H) 3.85-3.89 (m, 10H), 3.99-4.02 (m, 4H), 5.90 (br s, 1H), 6.48 (t, 1H), 6.90 (d, 1H), 7.29-7.38 (m, 2H), 7.90 (s, 1H), 7.99 (d, 1H), 8.30 (d, 2H); MS (ESI⁺) 490 (MH⁺).

15: 3-[6-(4-Cyclohexylmethyl-piperazin-1-ylmethyl)-4-morpholin-4-yl-thieno[3,2-d]pyrimidin-2-yl]-phenol was prepared using 1-(cyclohexylmethyl)piperazine.

¹H NMR (400 MHz, CDCl₃) 0.83-0.95 (2H, m), 1.17-1.26 (3H, m), 1.42-1.50 (1H, m), 1.68-1.77 (5H, m), 2.14 (2H, d, J=7.1 Hz), 2.40-2.50 (4H, br m), 2.52-2.64 (4H, broad), 3.81 (2H, s), 3.87 (4H, t, J=4.6 Hz), 4.03 (4H, t, J=4.6 Hz), 5.23-5.28 (1H, broad, OH), 6.92-6.94 (1H, m), 7.31 (1H, s), 7.33 (1H, t, J=7.9 Hz), 7.91 (1H, s), 8.00 (1H, d, J=7.8); MS (ESI⁺) 508.2 (MH⁺).

16: 3-[6-(4-Isopropyl-piperazin-1-ylmethyl)-4-morpholin-4-yl-thieno[3,2-d]pyrimidin-2-yl]-phenol was prepared using 1-isopropylpiperazine.

¹H NMR (400 MHz, d₆-DMSO) 0.99 (d, 6H), 2.65 (septet, 1H) 3.82-3.88 (m, 6H), 3.94-3.99 (m, 4H), 6.90 (d, 1H), 7.27-7.30 (m, 1H), 7.40 (s, 1H), 7.84-7.88 (m, 2H), 9.55 (1H, s), 8H hidden under DMSO peak @ 2.52; MS (ESI⁺) 454 (MH⁺).

17: 4-[2-(3-Hydroxy-phenyl)-4-morpholin-4-yl-thieno[3,2-d]pyrimidin-6-ylmethyl]-piperazine-1-carboxylic acid tert-butyl ester was prepared using 1-BOC-piperazine.

¹H NMR (400 MHz, CDCl₃) 1.48 (s, 9H) 2.48-2.52 (m, 4H), 3.48-3.51 (m, 4H), 3.79 (s, 2H), 3.85-3.89 (m, 4H), 3.99-4.02 (m, 4H) 6.90 (d, 1H), 7.29-7.38 (m, 2H), 7.76-7.99 (m, 2H); MS (ESI⁺) 512 (MH⁺).

19: 3-{6-[4-(2-Methoxy-ethyl)-piperazin-1-ylmethyl]-4-morpholin-4-yl-thieno[3,2-d]pyrimidin-2-yl}-phenol was prepared using 1-(2-methoxyethyl)piperazine.

¹H NMR (400 MHz, CDCl₃) 2.58-2.68 (m, 10H), 3.35 (s, 3H), 3.52 (t, 2H, J=5.6 Hz), 3.82 (s, 2H), 3.87 (t, 4H, J=4.6 Hz), 4.03 (t, 4H, J=4.6 Hz), 5.60-5.68 (brs, 1H), 6.92-6.94 (m, 1H), 7.31 (s, 1H), 7.33 (t, 1H, J=7.9), 7.91 (s, 1H), 8.00 (d, 1H, J=7.8 Hz). MS (ESI⁺) 470.1 (MH⁺).

20: 3-[6-(4-Methyl-[1,4]diazepan-1-ylmethyl)-4-morpholin-4-yl-thieno[3,2-d]pyrimidin-2-yl]-phenol was prepared using 1-methylhomopiperazine.

¹H NMR (400 MHz, CDCl₃) 1.85-1.89 (m, 2H), 2.40 (s, 3H), 2.65-2.74 (m, 4H), 2.82-2.86 (m, 4H), 3.88 (t, 4H, J=4.6 Hz), 3.95 (s, 2H), 4.04 (t, 4H, J=4.6 Hz), 5.90-5.98 (br s, 1H), 6.92-6.94 (m, 1H), 7.31 (s, 1H), 7.33 (t, 1H, J=7.9 Hz), 7.91 (s, 1H), 8.00 (d, 1H, J=7.8 Hz); MS (ESI⁺) 440.1 (MH⁺).

21: {4-[2-(3-Hydroxy-phenyl)-4-morpholin-4-yl-thieno[3,2-d]pyrimidin-6-ylmethyl]-piperazin-1-yl}-acetic acid ethyl ester was prepared from 1-ethoxycarbonylmethyl)piperazine.

¹H NMR (400 MHz, CDCl₃) 1.27 (t, 3H, J=7.1 Hz), 2.60-2.69 (br, 8H), 3.23 (s, 2H), 3.83 (s, 2H), 3.89 (t, 4H, J=4.6 Hz), 4.03 (t, 4H, J=4.6 Hz), 4.20 (q, 2H, J=4.6 Hz), 5.12 (brs, 1H), 6.92-6.94 (m, 1H), 7.31 (s, 1H), 7.33 (t, 1H, J=7.9), 7.91 (s, 1H), 8.00 (d, 1H, J=7.8 Hz); MS (ESI⁺) 498.1 (MH⁺)

22: 1-{4-[2-(3-Hydroxy-phenyl)-4-morpholin-4-yl-thieno[3,2-d]pyrimidin-6-ylmethyl]-piperazin-1-yl}-ethanone was prepared from 1-acetylpiperazine.

¹H NMR (400 MHz, CDCl₃) 2.09 (s, 3H, CH₃), 2.52-2.55 (m, 4H, 2×CH₂), 3.49-3.51 (m, 2H, CH₂), 3.66-3.68 (m, 2H, CH₂), 3.83 (s, 2H, CH₂), 3.86-3.90 (m, 4H, 2×CH₂), 4.03-4.06 (m, 4H, 2×CH₂), 5.88 (br s, H, OH), 6.94 (d, H, ArH, J=7.66 Hz), 7.31-7.35 (m, 2H, 2×ArH), 7.93 (s, H, ArH), 7.98 (d, H, ArH, J=7.77 Hz); MS (ESI⁺) 454.0 (MH⁺).

23: 3-{6-[4-(2-Hydroxy-ethyl)-piperazin-1-ylmethyl]-4-morpholin-4-yl-thieno[3,2-d]pyrimidin-2-yl}-phenol was prepared from N-(2-hydroxyethyl)piperazine.

¹H NMR (400 MHz, CDCl₃) 2.63 (br m, 10H, 2×CH₂), 3.65 (m, 2H, CH₂), 3.84 (s, 2H, CH₂), 3.87-3.90 (m, 4H, 2×CH₂), 4.04-4.06 (m, 4H, 2×CH₂), 6.93 (d, H, ArH, J=10.0 Hz), 7.32-7.36 (m, 2H, 2×ArH), 7.91 (s, H, ArH), 8.01 (d, H, ArH, J=7.74 Hz); MS (ESI⁺) 456.1 (MH⁺).

24: 3-(4-Morpholin-4-yl-6-thiomorpholin-4-ylmethyl-thieno[3,2-d]pyrimidin-2-yl)-phenol was prepared from thiomorpholine.

¹H NMR (400 MHz, CDCl₃) 2.70-2.72 (m, 4H, 2×CH₂), 2.80-2.82 (m, 4H, 2×CH₂), 3.83 (s, 2H, CH₂), 3.87-3.90 (m, 4H, 2×Cl₂), 5.77 (sbr, H, OH), 6.93 (d, H, ArH, J=7.84 Hz), 7.30-7.35 (m, 2H, 2×ArH), 7.93 (s, H, ArH), 7.98 (d, H, ArH, J=7.84 Hz); MS (ESI⁺) 429.2 (MH⁺).

25: 3-[6-(4-Ethyl-piperazin-1-ylmethyl)-4-morpholin-4-yl-thieno[3,2-d]pyrimidin-2-yl]-phenol was prepared from 1-ethylpiperazine.

¹H NMR (400 MHz, CDCl₃) 1.11 (t, 3H, J=7.1 Hz), 2.45-2.49 (br m, 2H), 2.49-2.72 (br, 8H), 3.83 (s, 2H), 3.88 (t, 4H, J=4.6 Hz), 4.03 (t, 4H, J=4.6 Hz), 6.24-6.32 (br, 1H), 6.91-6.94 (m, 1H), 7.28 (s, 1H), 7.33 (t, 1H, J=7.9 Hz), 7.94 (s, 1H), 7.98 (d, 1H, J=7.8 Hz); MS (ESI⁺) 440.2 (MH⁺).

26: 3-(6-{[Methyl-(1-methyl-piperidin-4-yl)-amino]-methyl}-4-morpholin-4-yl-thieno[3,2-d]pyrimidin-2-yl)-phenol was prepared from 1-methyl-4-(methylamino)piperidine.

¹H NMR (400 MHz, CDCl₃) 1.80-1.88 (3H, br m), 1.97-2.08 (1H, br m), 2.17 (3H, s), 2.33 (3H, s), 2.33-2.39 (2H, br m), 2.48-2.56 (1H, br m), 2.99-3.10 (2H, br m), 3.83 (2H, s), 3.86-3.89 (4H, m), 4.02-4.04 (4H, m), 6.93 (1H, m), 7.21 (1H, s), 7.32 (1H, t, J=7.9), 7.93 (1H, s), 8.00 (1H, d, J=7.8); MS (ESI⁺) 454.1 (MH⁺)

27: 3-[6-(4-Dimethylamino-piperidin-1-ylmethyl)-4-morpholin-4-yl-thieno[3,2-d]pyrimidin-2-yl]-phenol was prepared from 4-dimethylaminopiperidine.

¹H NMR (400 MHz, CDCl₃) 1.58-1.68 (br m, 2H), 1.87-1.95 (br m, 2H), 2.10 (br t, 2H, J=10.7 Hz), 2.34 (br m, 1H), 2.37 (br s, 6H), 3.02 (br m, 2H), 3.80 (s, 2H), 3.87 (t, 4H, J=4.7 Hz), 4.03 (t, 4H, J=4.9 Hz), 6.92-6.94 (m, 1H), 7.31 (s, 1H), 7.33 (t, 1H, J=7.9 Hz), 7.91 (s, 1H), 8.00 (d, 1H, J=7.8 Hz); MS (ESI⁺) 454.1 (MH⁺).

28: 4-[2-(3-Hydroxy-phenyl)-4-morpholin-4-yl-thieno[3,2-d]pyrimidin-6-ylmethyl]-piperazin-2-one was prepared from piperazin-2-one.

¹H NMR (400 MHz, CDCl₃) 2.77 (t, 2H, J=5.3 Hz), 3.39 (2H, s), 3.42 (br t, 2H), 3.89 (t, 4H, J=5.0 Hz), 3.92 (s, 2H), 4.05 (t, 4H, J=5.0 Hz), 5.48 (br s, 1H), 5.86 (bs, 1H), 6.92-6.94 (m, 1H), 7.31 (s, 1H), 7.33 (t, 1H, J=7.9 Hz), 7.91 (s, 1H), 8.00 (d, 1H, J=7.8 Hz); MS (ESI⁺) 426.1 (MH⁺).

29: 3-[6-(4-Methanesulfonyl-piperazin-1-ylmethyl)-4-morpholin-4-yl-thieno[3,2-d]pyrimidin-2-yl]-phenol was prepared from 1-methanesulfonylpiperazine hydrochloride. This in turn was prepared by reaction of N—BOC-piperazine with methane sulfonyl chloride in dichloromethane, followed by cleavage of the BOC protecting group using HCl (2M) in dichloromethane.

¹H NMR (400 MHz, CDCl₃) 2.59 (m, 4H, 2×CH₂), 2.72 (s, 3H, CH₃), 3.20 (m, 4H, 2×CH₂), 3.80 (m, 6H, 3×CH₂), 3.94-3.97 (m, 4H, 2×CH₂), 6.87 (d, H, ArH, J=7.76 Hz), 7.19-7.27 (m, 2H, 2×ArH), 7.88 (m, 2H, 2×ArH); MS (ESI⁺) 490.0 (MH⁺).

30: {4-[2-(3-Hydroxy-phenyl)-4-morpholin-4-yl-thieno[3,2-d]pyrimidin-6-ylmethyl]-piperazin-1-yl}-acetonitrile was prepared from piperazin-1-yl-acetonitrile hydrochloride. This in turn was prepared from prepared by reaction of N—BOC-piperazine with bromoacetonitrile in MeCN, followed by cleavage of the BOC protecting group using HCl (2M) in dichloromethane.

¹H NMR (400 MHz, CDCl₃) 2.64-2.68 (m, 8H, 4×CH₂), 3.56 (s, 2H, CH₂), 3.84 (s, 2H, CH₂), 3.90-3.92 (m, 4H, 2×CH₂), 4.05-4.08 (m, 4H, 2×CH₂), 6.93-6.95 (m, H, ArH), 7.32-7.36 (m, 2H, 2×ArH), 7.94 (s, H, ArH), 8.0 (d, H, ArH, J=7.8 Hz). MS (ESI⁺) 451.1 (MH⁺).

31: 3-[4-Morpholin-4-yl-6-(4-morpholin-4-yl-piperidin-1-ylmethyl)-thieno[3,2-d]pyrimidin-2-yl]-phenol was prepared from 4-morpholinopiperidine.

¹H NMR (400 MHz, CDCl₃) 1.56-1.65 (m, 2H, CH₂), 1.83-1.86 (m, 2H, CH₂), 2.08-2.14 (m, 2H, CH₂), 2.19-2.24 (m, H, CH), 2.55 (m, 4H, 2×CH₂), 3.02-3.05 (m, 2H, CH₂), 3.72-3.74 (m, 4H, 2×CH₂), 3.79 (s, 2H, CH₂), 3.85-3.88 (m, 4H, 2×CH₂), 4.0-4.03 (m, 4H, 2×CH₂), 6.52 (br s, H, OH), 6.91 (m, H, ArH), 7.29-7.34 (m, 2H, 2×ArH), 7.91 (s, H, ArH), 7.98 (d, H, ArH, J=7.8 Hz); MS (ESI⁺) 496.2 (MH⁺).

33: 3-[6-(3-Dimethylamino-pyrrolidin-1-ylmethyl)-4-morpholin-4-yl-thieno[3,2-d]pyrimidin-2-yl]-phenol was prepared from 3-(dimethylamino) pyrrolidine.

¹H NMR (400 MHz, d₆-DMSO) 9.52 (s, 1H), 7.85 (m, 2H), 7.37 (s, 1H), 7.28 (t, 1H, J=7.6 Hz), 6.87 (d, 1H), 3.96 (m, 6H), 3.82 (m, 4H), 2.89 (m, 2H), 2.79 (m, 1H), 2.68 (m, 1H), 2.24 (s, 6H), 1.95 (m, 1H), 1.74 (m, 1H); MS (ESI⁺) 440.1 (MH⁺).

34: 1-[2-(3-Hydroxy-phenyl)-4-morpholin-4-yl-thieno[3,2-d]pyrimidin-6-ylmethyl]-4-morpholin-4-ylmethyl-piperidin-4-ol was prepared from 4-morpholin-4-ylmethyl-piperidin-4-ol dihydrochloride. This was prepared as follows: trimethylsulfoxonium iodide (1.0 g, 4.54 mmol, 1.03 eq.) and sodium hydride (190 mg, 4.75 mmol, 1.08 eq.) were stirred in dry DMSO (5 mL) under nitrogen. After 30 min. a solution of t-butyl 4-oxo-1-piperidine carboxylate (875 mg, 4.39 mmol, 1 eq.) in DMSO was added and the resultant heated at 60° C. under argon for 4 hours. The mixture was then cooled, diluted with water and extracted with EtOAc (3×30 mL). The combined extracts were dried (Na₂SO₄) and purified by flash chromatography (silica gel, 20% EtOAc/Hexanes) to give 1-oxa-6-aza-spiro[2.5]octane-6-carboxylic acid tert-butyl ester as an off-white solid (661.6 mg, 71%).

1-Oxa-6-aza-spiro[2.5]octane-6-carboxylic acid tert-butyl ester (100 mg, 0.47 mmol) and morpholine (42 µL, 0.48 mmol, 1.03 eq) were stirred in EtOH at RT overnight. Solvent was removed in vacuo and the residue purified by flash chromatography (silica gel, 4% MeOH/DCM) to give 4-hydroxy-4-morpholin-4-ylmethyl-piperidine-1-carboxylic acid tert-butyl ester as a white solid (91.4 mg, 67%).

To a solution of 4-hydroxy-4-morpholin-4-ylmethyl-piperidine-1-carboxylic acid tert-butyl ester (91.4 mg, 0.32 mmol) in MeOH (3 mL) was added 2 M HCl in ether (480 µL, 0.96 mmol, 3 eq.). The mixture was stirred at RT for 4 days then concentrated in vacuo to give a gum which was used without further purification.

¹H NMR (400 MHz, CDCl₃) 1.56-1.62 (m, 4H, 2×CH₂, part HOD), 2.35 (s, 2H, CH₂), 2.51 (m, 2H, CH₂), 2.61-2.64 (m, 4H, 2×CH₂), 2.74 (m, 2H, CH₂), 3.12 (br s, H, OH), 3.69-3.71 (m, 4H, 2×CH₂), 3.84 (s, 2H, CH₂), 3.87-3.89 (m, 4H, 2×CH₂), 4.02-4.05 (m, 4H, 2×CH₂), 5.2 (br s, H, OH), 6.94 (d, H, ArH, J=7.55 Hz), 7.31 (s, H, ArH), 7.35 (t, H, ArH, J=7.9 Hz), 7.9 (s, H, ArH), 8.02 (d, H, ArH, J=7.75 Hz); MS (ESI⁺), 526.2 (MH⁺+OMe)

35: 4-[2-(3-Hydroxy-phenyl)-4-morpholin-4-yl-thieno[3,2-d]pyrimidin-6-ylmethyl]-piperazine-1-carboxylic acid ethylamide was prepared from piperazine-1-carboxylic acid ethylamide. This in turn was prepared by reaction of N—BOC-piperazine with ethyl isocyanate in dichloromethane, followed by cleavage of the BOC protecting group using HCl (2M solution in ether) in dichloromethane.

¹H NMR (400 MHz, CDCl₃) 1.14 (t, 3H, J=7.3 Hz), 2.55 (t, 4H, J=5.0 Hz), 3.25-3.32 (m, 2H), 3.41 (t, 4H, J=5.0 Hz), 3.84 (s, 2H), 3.89 (t, 4H, J=4 Hz), 4.05 (t, 4H, J=4.8 Hz), 4.35 (t, 1H), 5.22-5.28 (br m, 1H), 6.92-6.94 (m, 1H), 7.31 (s, 1H), 7.33 (t, 1H, J=7.9 Hz), 7.91 (s, 1H), 8.00 (d, 1H, J=7.8 Hz); MS (ESI⁺) 483.1 (MH⁺).

39: 4-[2-(3-Hydroxy-phenyl)-4-morpholin-4-yl-thieno[3,2-d]pyrimidin-6-ylmethyl]-piperazine-1-carboxylic acid dimethylamide was prepared from piperazine-1-carboxylic acid dimethylamide.

¹H NMR (400 MHz, d₆-DMSO) 9.50 (1H, br s), 7.85-7.80 (2H, m), 7.38 (1H, s), 7.30-7.27 (1H, m), 6.85 (1H, d), 3.99-3.96 (4H, m), 3.90 (2H, s), 3.81-3.78 (4H, m), 3.17-3.15 (4H, m), 2.72 (6H, s), 2.55-2.52 (4H, m); MS (ESI⁺) 483 (MH⁺).

40: 1-[2-(3-Hydroxy-phenyl)-4-morpholin-4-yl-thieno[3,2-d]pyrimidin-6-ylmethyl]-piperidin-4-ol was prepared from 4-hydroxypiperidine.

¹H NMR (400 MHz, d₆-DMSO) 1.40-1.47 (m, 2H), 1.72-1.75 (m, 2H), 2.16-2.21 (m, 2H), 2.75-2.78 (m, 2H), 3.48-3.50 (m, 1H), 3.79-3.82 (m, 6H), 3.96-3.98 (m, 4H), 4.57 (d, 1H, J=4.1 Hz), 6.85 (dd, 1H), 7.26 (t, 1H, J=8.1 Hz), 7.35 (s, 1H), 7.83-7.85 (m, 2H), 9.48 (s, 1H); MS (ESI⁺) 427.1 (MH⁺).

41: 3-[6-(1,1-Dioxo-thiomorpholin-4-ylmethyl)-4-morpholin-4-yl-thieno[3,2-d]pyrimidin-2-yl]-phenol was prepared from thiomorpholine 1,1-dioxide, which in turn was prepared according to the literature (Journal of Medicinal Chemistry, 1994, 37, 913-923).

¹H NMR (400 MHz, d₆-DMSO) 9.50 (br s, 1H), 7.85-7.80 (m, 2H), 7.40 (1H, s), 7.30-7.27 (m, 1H), 6.85 (d, 1H), 4.08 (s, 2H), 4.00-3.95 (m, 4H), 3.81-3.78 (m, 4H), 3.23-3.20 (m, 4H), 3.02-2.98 (m, 4H); MS (ESI⁺) 461 (MH⁺).

42: 4-[2-(3-Hydroxy-phenyl)-4-morpholin-4-yl-thieno[3,2-d]pyrimidin-6-ylmethyl]-piperazine-1-sulfonic acid dimethylamide was prepared using piperazine-1-sulfonic acid dimethylamide.

¹H NMR (400 MHz, d₆-DMSO) 9.50 (1H, br s), 7.85-7.80 (2H, m), 7.40 (1H, s), 7.30-7.27 (1H, m), 6.85 (1H, d), 4.02-3.98 (4H, m), 3.95 (2H, s), 3.81-3.78 (4H, m), 3.23-3.20 (4H, m), 2.75 (6H, s), 2.55-2.52 (4H, m); MS (ESI⁺) 519.4 (MH⁺).

43: 3-(6-{4-[(2-Methoxy-ethyl)-methyl-amino]-piperidin-1-ylmethyl}-4-morpholin-4-yl-thieno[3,2-d]pyrimidin-2-yl)-phenol was prepared from (2-methoxy-ethyl)-methyl-piperidin-4-yl-amide. This in turn was prepared from tert-butyl-4-oxo-1-piperidine carboxylate and N-(2-methoxyethyl)methylamine via reductive amination, followed by cleavage of the BOC protecting group using HCl (2M solution in ether) in dichloromethane.

¹H NMR (400 MHz, d₆-DMSO) 1.40-1.49 (m, 2H), 1.64-1.67 (m, 2H), 2.02-2.07 (m, 2H), 2.20 (s, 3H), 2.29-2.35 (m, 1H), 2.56 (t, 2H, J=6.2 Hz), 2.93-2.96 (m, 2H), 3.23 (s, 3H), 3.36 (t, 2H, J=6.2 Hz), 3.79-3.82 (m, 6H), 3.96-3.98 (m, 4H), 6.85 (dd, 1H), 7.26 (t, 1H, J=8.1 Hz), 7.35 (s, 1H), 7.83-7.85 (m, 2H), 9.48 (s, 1H); MS (ESI⁺) 498.2 (MH⁺)

44: 1-[2-(3-Hydroxy-phenyl)-4-morpholin-4-yl-thieno[3,2-d]pyrimidin-6-ylmethyl]-pyrrolidin-3-ol was prepared from 3-pyrrolidinol.

$^1$H NMR (400 MHz, d$_6$-DMSO) 1.59 (m, 1H), 2.00 (m, 1H), 2.45 (m, 1H), 2.50 (m, 1H), 2.69 (m, 1H), 2.84 (m, 1H), 3.80 (m, 4H), 3.96 (m, 6H), 4.24 (s, 1H), 4.74 (br s, 1H), 6.85 (m, 1H), 7.26 (t, 1H, J=7.9 Hz), 7.34 (s, 1H), 7.83 (br s, 2H), 9.45 (s, 1H); MS (ESI$^+$) 413.1 (MH$^+$).

45: (R,S)-3-[6-(2-Dimethylaminomethyl-pyrrolidin-1-yl-methyl)-4-morpholin-4-yl-thieno[3,2-d]pyrimidin-2-yl]-phenol was prepared from (R,S)-Dimethyl-(1-methyl-pyrrolidin-2-ylmethyl)-amine, which was prepared by standard methods (*J. Med. Chem.* 2002, 45, 721)

$^1$H NMR (400 MHz, CDCl$_3$) 1.64-1.78 (m, 3H), 2.01 (m, 1H), 2.28 (s, 6H, & m, 1H), 2.34 (dd, 1H, J=12.3 Hz, 7.3 Hz), 2.53 (dd, 1H, J=12.3 Hz, 4.7 Hz), 3.10 (m, 1H), 2.70 (m, 1H), 3.71 (d, 1H, J=14.6 Hz), 3.88 (t, 4H, J=4.8 Hz), 4.03 (t, 4H, J=4.8 Hz), 4.42 (d, 1H, J=14.7), 6.92 (dd, 1H, J=7.7 Hz, 2.3 Hz), 7.26 (s, 1H), 7.33 (t, 1H, J=7.9 Hz), 7.91 (t, 1H, J=1.9 Hz), 8.00 (d, 1H, J=7.8 Hz); MS (ESI$^+$) 454.4 (MH$^+$).

46: (R,S)-3-(6-{[Methyl-(1-methyl-pyrrolidin-2-ylmethyl)-amino]-methyl}-4-morpholin-4-yl-thieno[3,2-d]pyrimidin-2-yl)-phenol was prepared from (R,S)-methyl-(1-methyl-pyrrolidin-2-ylmethyl)-amine prepared in turn as follows: 1-methyl-2-pyrrolecarboxaldehyde (1.0 g, 9.16 mmol) was added to a solution of methyl amine in methanol (2.31 g in 10 mL) and the mixture stirred at room temperature for 3.5 hours. The solution was cooled in ice-water and sodium borohydride added (2.0 eq., 18.3 mmol, 693 mg) and then stirred at room temperature for 17 hours. The solvent was evaporated and the residue partitioned between saturated aqueous sodium hydrogen carbonate (30 mL) and dichloromethane (3×30 mL). The combined organic layers were washed with brine, separated and dried (MgSO$_4$). Hydrogenation over platinum oxide (*Chem. Pharm. Bull.*, 1990, 38, 930-935) furnished the desired compound.

$^1$H NMR (400 MHz, CDCl$_3$) 1.59-1.76 (m, 3H), 1.97 (m, 1H), 2.17 (dd, 1H, J=17.4 Hz, 9.5 Hz), 2.23 (s, 3H), 2.34-2.40 (m, 2H), 2.40 (s, 3H), 2.65 (dd, 1H, J=11.5 Hz, 4.1 Hz), 3.05 (t, 1H, J=7.5 Hz), 7.85 (d, 1H, J=7.9 Hz), 3.72-3.77 (m, 6H), 3.89 (t, 4H, J=4.8 Hz), 6.79 (dt, 1H, J=6.2 Hz, 1.2 Hz), 7.22 (m, 2H), 7.79 (t, 1H, J=1.9 Hz); MS (ESI$^+$) 454.4 (MH$^+$).

47: 1-[2-(3-Hydroxy-phenyl)-4-morpholin-4-yl-thieno[3,2-d]pyrimidin-6-ylmethyl]-piperidine-4-carboxylic acid amide was prepared from isonipecotamide.

$^1$H NMR (400 MHz, d$_6$-DMSO) 1.55-1.71 (m, 4H), 2.03-2.10 (m, 3H), 2.91-2.94 (m, 2H), 3.79-3.83 (m, 6H), 3.96-3.99 (m, 4H), 6.73 (br s, 1H), 6.85 (d, 1H), 7.23-7.28 (m, 2H), 7.36 (s, 1H), 7.83-7.85 (m, 2H), 9.48 (s, 1H); MS (ESI$^+$) 454.1 (MH$^+$).

48: 2-{4-[2-(3-Hydroxy-phenyl)-4-morpholin-4-yl-thieno[3,2-d]pyrimidin-6-ylmethyl]-piperazin-1-yl}-N,N-dimethylacetamide was prepared from N,N-dimethyl-2-piperazin-1-yl-acetamide dihydrochloride. This in turn was prepared by reaction of N—BOC-piperazine with 2-chloro-N,N-dimethylacetamide in dichloromethane, followed by cleavage of the BOC protecting group using HCl (2M) in dichloromethane.

$^1$H NMR (400 MHz, CDCl$_3$) 2.61 (br s, 8H, 4×CH$_2$), 2.94 (s, 3H, CH$_3$), 3.07 (s, 3H, CH$_3$), 3.19 (s, 2H, CH$_2$), 3.81 (s, 2H, CH$_2$), 3.86-3.88 (m, 4H, 2×CH$_2$), 4.02-4.04 (m, 4H, 2×CH$_2$), 5.61 (br s, H, OH), 6.92 (d, H, ArH, J=7.56 Hz), 7.28 (s, H, ArH), 7.31 (t, H, ArH, J=6.9 Hz), 7.9 (s, H, ArH), 7.98 (d, H, ArH, J=7.82 Hz); MS (ESI$^+$) 497.1 (MH$^+$).

49: 3-(6-{[Methyl-(1-methyl-pyrrolidin-3-yl)-amino]-methyl}-4-morpholin-4-yl-thieno[3,2-d]pyrimidin-2-yl)-phenol was prepared from N,N'-dimethyl-3-aminopyrrolidine.

$^1$H NMR (400 MHz, d$_6$-DMSO) 1.72 (m, 1H), 1.94 (m, 1H), 2.19 (s, 3H), 2.25 (s, 3H), 2.42 (m, 1H), 2.58 (m, 2H), 3.18 (m, 2H), 3.79 (m, 4H), 3.86 (s, 2H), 3.96 (m, 4H), 6.85 (dd, 1H, J=6.9 Hz), 7.26 (t, 1H, J=7.7 Hz), 7.35 (s, 1H), 7.82 (s, 1H), 7.84 (s, 1H), 9.46 (s, 1H); MS (ESI$^+$) 440.1 (MH$^+$).

50: 2-Dimethylamino-1-{4-[2-(3-hydroxy-phenyl)-4-morpholin-4-yl-thieno[3,2-d]pyrimidin-6-ylmethyl]-piperazin-1-yl}-ethanone was prepared from 2-dimethylamino-1-piperazin-1-yl-ethanone. This in turn was prepared from 1-BOC-piperazine and bromoacetyl bromide in dichloromethane, followed by reaction with dimethylamine hydrochloride and subsequent deprotection of the BOC-group using HCl (2M solution in ether) in dichloromethane.

$^1$H NMR (400 MHz, CDCl$_3$) 2.28 (s, 6H), 2.53-2.55 (m, 4H), 3.12 (s, 2H), 3.65-3.67 (4H, br m), 3.83 (2H, s), 3.87-3.90 (4H, m), 4.04-4.06 (4H, m), 6.92 (1H, m), 7.31 (1H, s), 7.33 (t, 1H, J=7.9 Hz), 7.93 (s, 1H), 8.00 (d, 1H, J=7.8 Hz); MS (ESI$^+$) 497.1 (MH$^+$).

51: 3-[6-((3R,5S)-3,5-Dimethyl-piperazin-1-ylmethyl)-4-morpholin-4-yl-thieno[3,2-d]pyrimidin-2-yl]-phenol was prepared from 2,6-dimethylpiperazine.

$^1$H NMR (400 MHz, d$_6$-DMSO) 0.97 (s, 6H), 1.74 (br m, 2H), 2.80-2.82 (br m, 2H), 2.90 (br m, 2H), 3.79-3.81 (m, 4H), 3.83 (s, 2H), 3.95-3.97 (m, 4H), 6.84-6.88 (m, 1H), 7.26 (t, 1H, J=8.0 Hz), 7.37 (s, 1H), 7.82-7.85 (m, 2H), 9.46 (br s, 1H); MS (ESI$^+$) 440.1 (MH$^+$).

54: 3-{6-[4-(3-Dimethylamino-propane-1-sulfonyl)-piperazin-1-ylmethyl]-4-morpholin-4-yl-thieno[3,2-d]pyrimidin-2-yl}-phenol was prepared from dimethyl-[3-(piperazine-1-sulfonyl)-propyl]-amine. This was prepared as follows: to a solution of N—BOC-piperazine (1.55 g, 8.32 mmol) in dry DCM was added triethylamine (1.28 mL, 9.18 mmol, 1.1 eq.) then 3-chloropropane sulfonyl chloride (1.1 mL, 9.05 mmol, 1.09 eq.). The mixture was stirred at rt overnight then diluted with CH$_2$Cl$_2$ and extracted washed with water (3×40 mL). The CH$_2$Cl$_2$ was dried (Na$_2$SO$_4$) then purified by flash chromatography (silica gel, 4% MeOH/CH$_2$Cl$_2$) to yield 4-(3-chloro-propane-1-sulfonyl)-piperazine-1-carboxylic acid tert-butyl ester as a white solid (2.68 g, 98%).

A mixture of 4-(3-chloro-propane-1-sulfonyl)-piperazine-1-carboxylic acid tert-butyl ester (152.6 mg, 0.47 mmol), dimethylamine hydrochloride (403.5 mg, 4.95 mmol, 10.6 eq.), potassium carbonate (72.7 mg, 0.53 mmol, 1.13 eq.) and triethylamine (690 µL, 4.95 mmol, 10.6 eq) in acetonitrile (10 mL) plus a catalytic amount of potassium iodide was heated at 80° C. in a sealed tube overnight. The solvent was then removed in vacuo. The residue diluted with water and extracted with CH$_2$Cl$_2$ (3×20 mL). The combined fractions were dried (Na$_2$SO$_4$) to yield 4-(3-dimethylamino-propane-1-sulfonyl)-piperazine-1-carboxylic acid tert-butyl ester as an orange solid (176 mg).

To a solution of 4-(3-dimethylamino-propane-1-sulfonyl)-piperazine-1-carboxylic acid tert-butyl ester (167 mg, 0.5 mmol) in dry CH$_2$Cl$_2$ (8 mL) was added 2 M HCl in ether (8 mL, 16 mmol, 32 eq.). The mixture was stirred at RT overnight. Solvent was then removed in vacuo and the residue used directly (163.5 mg, 100%).

$^1$H NMR (400 MHz, CDCl$_3$) 1.96-2.02 (m, 2H, 2×CH$_2$), 2.26 (s, 6H, 2×CH$_3$), 2.43 (t, 2H, CH$_2$, J=6.8 Hz), 2.54-2.56 (m, 4H, 2×CH$_2$), 2.95-2.99 (m, 2H, CH$_2$), 3.26-3.28 (m, 4H, 2×CH$_2$), 3.74 (s, 2H, CH$_2$), 3.80-0.88 (m, 4H, 2×CH$_2$), 4.01-4.03 (m, 4H, 2×CH$_2$), 6.88 (d, H, ArH, J=7.74 Hz), 7.24 (s, H,

ArH), 7.30 (t, H, ArH, J=7.88 Hz), 7.92 (m, H, ArH), 7.96 (d, H, ArH, J=7.82 Hz); MS (ESI$^+$) 561.1 (MH$^+$).

55: 3-[6-(4-Methoxy-piperidin-1-ylmethyl)-4-morpholin-4-yl-thieno[3,2-d]pyrimidin-2-yl]-phenol was prepared from 4-methoxypiperidine. This in turn was prepared by reaction of tert-butyl-4-hydroxy-1-piperidine carboxylate with methyl iodide, followed by cleavage of the BOC group using standard conditions;

$^1$H NMR (400 MHz, d$_6$-DMSO) 1.47 (m, 2H), 1.83 (m, 2H), 2.25 (m, 2H), 2.72 (m, 2H), 3.21 (s, 3H), 3.81 (m, 6H), 3.97 (m, 4H), 6.85 (m, 1H), 7.26 (t, 1H, J=8.1 Hz), 7.35 (s, 1H), 7.83 (m, 2H), 9.46 (s, 1H); MS (ESI$^+$) 441.1 (MH$^+$).

58: 3-{4-Morpholin-4-yl-6-[4-(3-morpholin-4-yl-propane-1-sulfonyl)-piperazin-1-ylmethyl]-thieno[3,2-d]pyrimidin-2-yl}-phenol was prepared from 4-[3-(piperazine-1-sulfonyl)-propyl]-morpholine. This was prepared in an analogous manner to dimethyl-[3-(piperazine-1-sulfonyl)-propyl]-amine using morpholine as the amine.

$^1$H NMR (400 MHz, CDCl$_3$) 1.98-2.04 (m, 2H, CH$_2$), 2.44-2.47 (m, 6H, 3×CH$_2$), 2.63-2.65 (m, 4H, 2×CH$_2$), 2.98-3.02 (m, 2H, CH$_2$), 3.33-3.35 (m, 4H, 2×CH$_2$), 3.68-3.71 (m, 4H, 2×CH$_2$), 3.85 (s, 2H, CH$_2$), 3.87-3.90 (m, 4H, 2×CH$_2$), 4.03-4.06 (m, 4H, 2×CH$_2$), 5.29 (br s, H, OH), 6.91-6.93 (m, H, ArH), 7.31-7.35 (m, 2H, 2×ArH), 7.91-7.92 (m, H, ArH), 7.99-8.01 (m, H, ArH); MS (ESI$^+$) 603.2 (MH$^+$).

57: {4-[2-(3-Hydroxy-phenyl)-4-morpholin-4-yl-thieno[3,2-d]pyrimidin-6-ylmethyl]-piperazin-1-yl}-morpholin-4-yl-methanone was prepared from morpholin-4-yl-piperazin-1-yl-methanone. This in turn was prepared by reaction of N—BOC-piperazine with 4-morpholino carbonyl chloride in acetonitrile, followed by cleavage of the BOC protecting group using HCl (2M) in dichloromethane.

$^1$H NMR (400 MHz, CDCl$_3$) 2.54-2.56 (m, 4H, 2×CH$_2$), 3.25-3.27 (m, 4H, 2×CH$_2$), 3.32-3.34 (m, 4H, 2×CH$_2$), 3.66-3.68 (m, 4H, 2×CH$_2$), 3.83 (s, 2H, CH$_2$), 3.87-3.89 (m, 4H, 2×CH$_2$), 4.03-4.05 (m, 4H, 2×CH$_2$), 5.33 (br s, H, OH), 6.91-6.93 (m, H, ArH), 7.30-7.34 (m, 2H, 2×ArH), 7.91-7.92 (m, H, ArH), 7.99-(d, H, ArH, J=7.82 Hz); MS (ESI$^+$) 525.1 (MH$^+$).

56: 4-[2-(3-Hydroxy-phenyl)-4-morpholin-4-yl-thieno[3,2-d]pyrimidin-6-ylmethyl]-piperazine-1-carboxylic acid (2-methoxy-ethyl)-methyl-amide was prepared from piperazine-1-carboxylic acid (2-methoxy-ethyl)-methyl-amide. This was prepared as follows:

To 1-BOC-piperazine (500 mg, 2.68 mmol) in dichloromethane (5 mL) and triethylamine (1.1 eq., 410 µL) was added 4-nitrophenylchloroformate (1 eq., 541 mg). After stirring at room temperature for 1 hour, the reaction mixture was diluted with dichloromethane, washed with brine, dried (MgSO$_4$), filtered and evaporated in vacuo to give piperazine-1,4-dicarboxylic acid tert-butyl ester 4-nitro-phenyl ester as a light-yellow solid (940 mg, 100%).

To piperazine-1,4-dicarboxylic acid tert-butyl ester 4-nitro-phenyl ester (500 mg, 1.42 mmol) in anhydrous THF (5 mL) was added N-(2-methoxy-ethyl)methylamine (2 eq., 254 mg). The reaction mixture was refluxed overnight, then evaporated in vacuo and purified by chromatography to give 4-[(2-methoxyethyl)-methyl-carbamoyl]piperazine-1-carboxylic acid tert-butyl ester as a clear oil (304 mg, 71%). To 4-[(2-methoxyethyl)-methyl-carbamoyl]piperazine-1-carboxylic acid tert-butyl ester (304 mg, 1.01 mmol) in dichloromethane (3 mL) was added HCl (2M solution in ether), the reaction mixture stirred at rt overnight and then evaporated in vacuo to give piperazine-1-carboxylic acid (2-methoxy-ethyl)-methyl-amide as HCl salt (330 mg).

$^1$H NMR (400 MHz, CDCl$_3$) 2.55-2.57 (m, 4H), 2.90 (s, 3H), 3.29-3.31 (m, 4H), 3.34 (s, 3H), 3.38 (t, 2H, J=5.5 Hz), 3.54 (t, 2H, J=5.5 Hz), 3.83 (s, 2H), 3.88-3.90 (m, 4H), 4.04-4.06 (m, 4H), 5.37 (brs, 1H), 6.93 (dd, 1H, J=7.8 Hz, 2.8 Hz), 7.26-7.35 (m, 2H), 7.93 (s, 1H), 8.01 (d, 1H, J=7.8 Hz); MS (ESI$^+$) 527.3 (MH$^+$).

Example 3

3-(4-Morpholin-4-yl-6-piperazin-1-ylmethyl-thieno[3,2-d]pyrimidin-2-yl)-phenol, trifluoroacetic acid salt (18)

To a solution of 4-[2-(3-hydroxy-phenyl)-4-morpholin-4-yl-thieno[3,2-d]pyrimidin-6-ylmethyl]-piperazine-1-carboxylic acid tert-butyl ester (95 mg) in dichloromethane (10 mL) was added trifluoroacetic acid (2 mL) After 3 hours the reaction mixture was concentrated in vacuo. Ether was added to the residue and the mixture was reduced in vacuo again to yield the title compound as a white foam.

$^1$H NMR (400 MHz, d$_6$-DMSO) 2.70-2.75 (m, 4H), 3.10-3.15 (m, 4H), 3.82-3.86 (m, 4H), 3.98-4.02 (m, 6H), 6.91 (d, 1H), 7.31-7.33 (m, 1H), 7.48 (s, 1H), 7.79-7.81 (m, 2H), 8.75 (br s, 2H), 9.60 (br s, 1H); MS (ESI$^+$) 412 (MH$^+$).

Example 4

1-{4-[2-(3-Hydroxy-phenyl)-4-morpholin-4-yl-thieno[3,2-d]pyrimidin-6-ylmethyl]-piperazin-1-yl}-2-methoxy-ethanone (37)

A mixture of 3-(4-morpholin-4-yl-6-piperazin-1-ylmethyl-thieno[3,2-d]pyrimidin-2-yl)-phenol, trifluoroacetic acid salt (50 mg, 0.08 mmol), dichloromethane (1 mL), triethylamine (45 µL) and methoxyacetyl chloride (19 µL, 2.5 eq.) was stirred at room temperature. After 3 hours the reaction mixture was diluted with dichloromethane, washed with sodium bicarbonate solution, dried (MgSO$_4$) and the solvent removed in vacuo to yield a pale solid. This was stirred in a mixture of methanol and sodium carbonate overnight. This mixture was then diluted with chloroform, washed with brine, dried (MgSO$_4$) and the solvent removed in vacuo to yield a gum which was purified using flash chromatography to yield the desired title compound (13 mg)

$^1$H NMR (400 MHz, CDCl$_3$) 7.99 (1H, d), 7.90 (1H, s), 7.38-7.29 (2H, m), 6.90 (1H, d), 5.20 (1H, br s), 4.10 (2H, s), 4.02-3.99 (4H, m), 3.89-3.85 (4H, m), 3.79 (2H, s), 3.75-3.73 (2H, m), 3.51-3.49 (2H, s), 3.40 (3H, s), 2.52-2.48 (4H, m); MS (ESI$^+$) 484 (MH$^+$).

Example 5

1-{(2R,6S)-4-[2-(3-hydroxy-phenyl)-4-morpholin-4-yl-thieno[3,2-d]pyrimidin-6-ylmethyl]-2,6-dimethyl-piperazin-1-yl}-ethanone (53)

To a solution of 2-[3-(tert-butyl-dimethyl-silanyloxy)-phenyl]-6-((3R,5S)-3,5-dimethyl-piperazin-1-ylmethyl)-4-morpholin-4-yl-thieno[3,2-d]pyrimidine (80 mg, 0.14 mmol) in dichloromethane (5 mL) was added triethylamine (40 µL, 2.0 equivalents) followed by acetyl chloride (15 µL, 1.5 eq.). After stirring overnight, the reaction mixture was diluted with dichloromethane, washed with aqueous sodium carbonate solution, dried (MgSO$_4$) and the solvent removed in vacuo to yield 1-((2R,6S)-4-{2-[3-(tert-butyl-dimethyl-silanyloxy)-phenyl]-4-morpholin-4-yl-thieno[3,2-d]pyrimidin-6-ylmethyl}-2,6-dimethyl-piperazin-1-yl)-ethanone (80 mg) as a white solid. Removal of the tert-butyldimethylsilyl protecting group was performed as described above to yield the title compound.

¹H NMR (400 MHz, d₆-DMSO; 373K) 1.29 (d, 6H), 1.99 (s, 3H), 2.28 (dd, 2H), 2.80 (d, 2H), 3.82-3.85 (m, 4H), 3.90 (s, 2H), 3.99-4.01 (m, 4H), 4.19-4.21 (m, 2H), 6.90 (d, 1H), 7.23-7.26 (m, 1H), 7.35 (s, 1H), 7.84-7.88 (m, 2H), 9.10 (brs, 1H). MS (ESI⁺) 482.1 (MH⁺)

Example 6

3-[6-((3R,5S)-4-Methanesulfonyl-3,5-dimethyl-piperazin-1-ylmethyl)-4-morpholin-4-yl-thieno[3,2-d]pyrimidin-2-yl]-phenol (52)

The title compound 52 was prepared by analogy with the process of Example 5, using methane sulfonyl chloride.
¹H NMR (400 MHz, CDCl₃/MeOD): 1.48 (s, 6H), 2.30 (br m, 2H), 2.76 (br m, 2H), 2.85 (s, 3H), 3.81 (s, 2H), 3.87 (br m, 4H), 4.04 (br m, 6H), 6.94 (br m, 1H), 7.26-7.29 (br m, 2H), 7.74 (br s, 1H), 7.86 (br m, 1H); MS (ESI⁺) 518.2 (MH⁺).

Example 7

3-[6-(4-Amino-piperidin-1-ylmethyl)-4-morpholin-4-yl-thieno[3,2-d]pyrimidin-2-yl]-phenol (32)

A mixture of (510 mg, 1.12 mmol), 4-(N—BOC-amino) piperidine (1.3 eq., 292 mg), acetic acid (1 eq., 65 μL) and sodium triacetoxyborohydride (1.5 eq., 357 mg) in 1,2-dichloroethane (7 mL) was stirred at RT overnight. The reaction mixture was diluted with dichloromethane, washed with saturated solution of sodium hydrogen carbonate, brine, separated and dried (MgSO₄). The crude product was evaporated in vacuo and purified by chromatography to give (1-{2-[3-(tert-butyl-dimethyl-silanyloxy)-phenyl]-4-morpholin-4-yl-thieno[3,2-d]pyrimidin-6-ylmethyl}-piperidin-4-yl)-carbamic acid tert-butyl ester (570 mg, 89%).
(1-{2-[3-(Tert-butyl-dimethyl-silanyloxy)-phenyl]-4-morpholin-4-yl-thieno[3,2-d]pyrimidin-6-ylmethyl}-piperidin-4-yl)-carbamic acid tert-butyl ester (250 mg, 0.39 mmol) was dissolved in THF (4 mL), to this was added TBAF (1.4 eq., 0.55 mL). After 30 min. the reaction mixture was quenched with silica, evaporated in vacuo and purified by chromatography to give {1-[2-(3-hydroxy-phenyl)-4-morpholin-4-yl-thieno[3,2-d]pyrimidin-6-ylmethyl]-piperidin-4-yl}-carbamic acid tert-butyl ester as a white solid (179 mg, 88%).
{1-[2-(3-Hydroxy-phenyl)-4-morpholin-4-yl-thieno[3,2-d]pyrimidin-6-ylmethyl]-piperidin-4-yl}-carbamic acid tert-butyl ester (179 mg, 0.34 mmol) was dissolved in dichloromethane (3 mL), to this was added HCl (2M solution in ether, 1 mL, excess). The reaction mixture stirred at room temperature for 1 hour and then evaporated in vacuo to give the title compound as di-HCl salt (197 mg).
¹H NMR (400 MHz, d₆-DMSO) 1.98-2.04 (br m, 2H), 2.11-2.18 (br m, 2H), 3.04-3.13 (br m, 2H), 3.25-3.28 (br m, 1H), 3.50-3.54 (br m, 2H), 3.83-3.87 (br m, 4H), 4.05-4.07 (br m, 4H), 4.70 (br s, 2H), 6.96 (d, 1H), 7.34 (t, 1H, J=7.8 Hz), 7.86 (1H, s), 7.88 (d, 1H), 7.95 (br s, 1H), 8.30 (br s, 3H), 9.70 (br s, 1H), 11.65 (br s, 1H); MS (ESI⁺) 426.1 (MH⁺).

Example 8

N-{1-[2-(3-Hydroxy-phenyl)-4-morpholin-4-yl-thieno[3,2-d]pyrimidin-6-ylmethyl]-piperidin-4-yl}-methanesulfonamide (36)

To 3-[6-(4-Amino-piperidin-1-ylmethyl)-4-morpholin-4-yl-thieno[3,2-d]pyrimidin-2-yl]-phenol di-hydrochloride salt (60 mg, 0.12 mmol) in DMF (1 mL) was added triethylamine (3 eq., 50 μL) and the reaction mixture stirred for 30 min. Next, methanesulfonic acid benzotriazol-1-yl ester (1.1 eq., 28 mg) was added and the mixture stirred at RT for 3 hours. Methanesulfonic acid benzotriazol-1-yl ester was prepared according to the procedure described in *Tetrahedron Lett.*, 1999, 40, 117-120.

The reaction mixture was diluted with dichloromethane, washed with brine, separated and dried (MgSO₄). The crude product was evaporated in vacuo, purified by chromatography to give the title compound as a white solid (39 mg, 80%).
¹H NMR (400 MHz, d₆-DMSO) 1.47-1.51 (m, 2H), 1.81-1.85 (m, 2H), 2.12-2.20 (m, 2H), 2.83-2.87 (m, 2H), 2.91 (s, 3H), 3.12-3.15 (m, 1H), 3.79-3.83 (m, 6H), 4.04-4.06 (m, 4H), 6.85 (d, 1H), 7.04 (d, 1H), 7.26 (t, 1H, J=8.1 Hz), 7.37 (s, 1H), 7.82-7.84 (m, 2H), 9.48 (s, 1H); MS (ESI⁺) 504.1 (MH⁺).

Example 9

N-{1-[2-(3-Hydroxy-phenyl)-4-morpholin-4-yl-thieno[3,2-d]pyrimidin-6-ylmethyl]-piperidin-4-yl}-acetamide (38)

To 3-[6-(4-Amino-piperidin-1-ylmethyl)-4-morpholin-4-yl-thieno[3,2-d]pyrimidin-2-yl]-phenol di-hydrochloride salt (80 mg, 0.16 mmol) in dichloromethane (1.5 mL) and triethylamine (5 eq., 110 μL) was added acetyl chloride (2.5 eq., 29 μL). After stirring at rt for 2 hours, the reaction mixture was diluted with dichloromethane, washed with brine, separated and dried (MgSO₄). The crude product was evaporated in vacuo, re-dissolved in methanol (2 mL), to this was added sodium carbonate. The reaction mixture was stirred at RT overnight, evaporated in vacuo, diluted with dichloromethane, washed with brine, separated and dried (MgSO₄). The residue was purified by chromatography to give the title compound as a white solid (55 mg).
¹H NMR (400 MHz, CDCl₃) 1.45-1.54 (m, 2H), 1.94-1.97 (m, 2H), 1.97 (s, 3H), 2.22-2.27 (m, 2H), 2.90-2.93 (m, 2H), 3.79 (s, 2H), 3.80-3.83 (m, 1H), 3.85-3.90 (m, 4H), 4.04-4.06 (m, 4H), 5.31 (d, 1H), 6.92-6.94 (m, 1H), 7.31 (s, 1H), 7.33 (t, 1H, J=7.9 Hz), 7.91 (s, 1H), 8.00 (d, 1H, J=7.8 Hz); MS (ESI⁺) 468.1 (MH⁺).

Reference Example 1

2,4-Dichloro-thieno[3,2-d]pyrimidine (64)

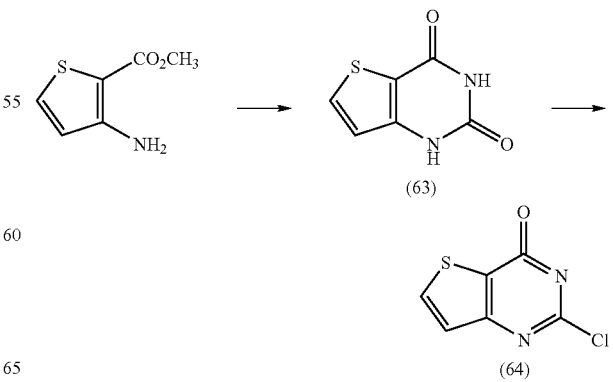

A mixture of methyl 3-amino-2-thiophenecarboxylate (13.48 g, 85.85 mmol) and urea (29.75 g, 5 eq.) was heated at 190° C. for 2 hours. The hot reaction mixture was then poured onto sodium hydroxide solution and any insoluble material removed by filtration. The mixture was then acidified (HCl, 2N) to yield 1H-thieno[3,2-d]pyrimidine-2,4-dione (63) as a white precipitate, which was collected by filtration and air dried (9.49 g, 66%).

$^1$H NMR (400 MHz, d$_6$-DMSO) 6.90 (1H, d, J=5.2 Hz), 8.10 (1H, d, J=5.2 Hz), 11.60-11.10 (2H, br, s).

A mixture of 1H-thieno[3,2-d]pyrimidine-2,4-dione (9.49 g, 56.49 mmol) and phosphorous oxychloride (150 mL) was heated at reflux for 6 hours. The reaction mixture was then cooled and poured onto ice/water with vigorous stirring yielding a precipitate. The mixture was then filtered to yield 2,4-dichloro-thieno[3,2-d]pyrimidine (64) as a white solid (8.68 g, 75%).

$^1$H NMR (400 MHz, CDCl$_3$) 7.56 (1H, d, J=5.5 Hz). 8.13 (1H, d, J=5.5 Hz).

Reference Example 2

2-Chloro-4-morpholin-4-yl-thieno[3,2-d]pyrimidine (65)

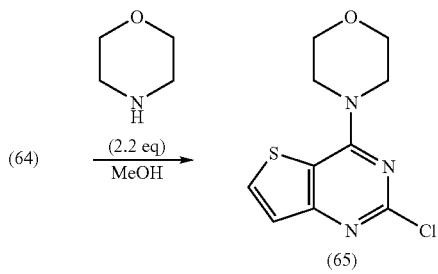

A mixture of 2,4-dichloro-thieno[3,2-d]pyrimidine (64), (8.68 g, 42.34 mmol), morpholine (8.11 mL, 2.2 eq.) and methanol (150 mL) was stirred at room temperature for 1 hour. The reaction mixture was then filtered, washed with water and methanol, to yield the title compound as a white solid (11.04 g, 100%).

$^1$H NMR (400 MHz, d$_6$-DMSO) 3.74 (4H, t, J=4.9 Hz), 3.90 (4H, t, J=4.9 Hz), 7.40 (1H, d, J=5.6 Hz), 8.30 (1H, d, J=5.6 Hz).

Reference Example 3

2-Chloro-4-morpholin-4-yl-thieno[3,2-d]pyrimidine-6-carbaldehyde (66)

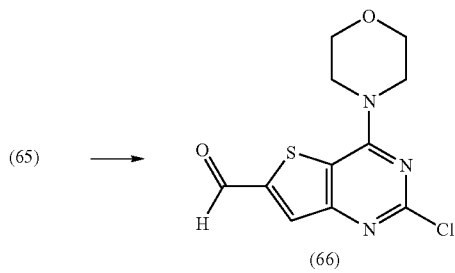

To a suspension of 2-chloro-4-morpholin-4-yl-thieno[3,2-d]pyrimidine (65) (1.75 g, 6.85 mmol) in dry THF (40 mL) at −78° C. was added a 2.5M solution of nBuLi in hexane (3.3 mL, 1.2 eq.). After stirring for 1 hour, dry N,N-dimethylformamide (796 μL, 1.5 eq.) was added. The reaction mixture was stirred for 1 hour at −78° C. and then warmed slowly to room temperature. After a further 2 hours at room temperature the reaction mixture poured onto ice/water yielding a yellow precipitate. This was collected by filtration and air-dried to yield the title compound (1.50 g, 77%).

$^1$H NMR (400 MHz, d$_6$-DMSO) 3.76 (4H, t, J=4.9 Hz), 3.95 (4H, t, J=4.9 Hz), 8.28 (1H, s), 10.20 (1H, s).

Reference Example 4

4-(4,4,5,5-Tetramethyl-[1,3,2]dioxaborolan-2-yl)-1H-indazole (70)

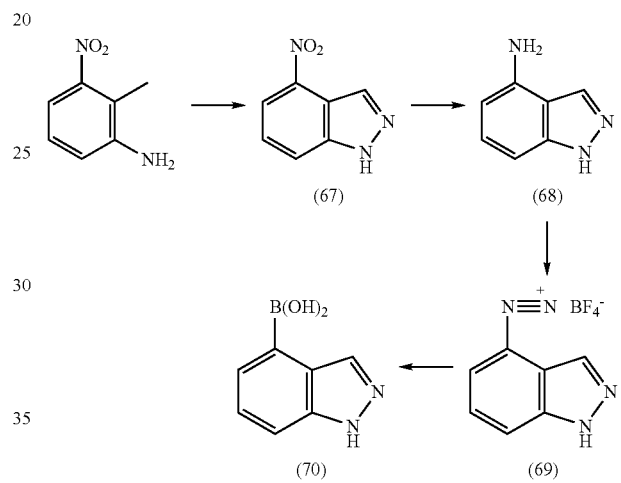

To a solution of 2-methyl-3-nitroaniline (2.27 g, 14.91 mmol) in acetic acid (60 mL) was added a solution of sodium nitrite (1.13 g, 1.1 eq.) in water (5 mL). After 2 hours, the deep red solution was poured onto ice/water and the precipitate collected by filtration to yield 4-nitro-1H-indazole (67) (1.98 g, 81%).

A mixture of 4-nitro-1H-indazole (760 mg, 4.68 mmol), palladium on charcoal (10%, cat.) and ethanol (30 mL) was stirred under a balloon of hydrogen for 4 hours. The reaction mixture was then filtered through celite, and the solvent removed in vacuo to yield 1H-indazol-4-ylamine (68) (631 mg, 100%).

An aqueous solution of sodium nitrite (337 mg, 4.89 mmol) in water (2 mL) was added dropwise to a suspension of 1H-indazol-4-ylamine (631 mg, 4.74 mmol) in 6M hydrochloric acid (7.2 mL) at below 0° C. After stirring for 30 minutes sodium tetrafluoroborate (724 mg) was added. The reaction mixture became very thick and was filtered and washed briefly with water to yield 1H-indazole-4-diazonium, tetrafluoroborate salt (69) (218 mg, 20%) as a deep red solid.

Dry methanol (4 mL) was purged with argon for 5 minutes. To this was added 1H-indazole-4-diazonium, tetrafluoroborate salt (218 mg, 0.94 mmol), bis-pinacolato diboron (239 mg, 1.0 eq.) and [1,1'-bis(diphenylphosphino)ferrocene]palladium(II) chloride (20 mg). The reaction mixture was stirred for 5 hours and then filtered through celite. The residue was purified using flash chromatography to yield the desired title compound (70), (117 mg).

Reference Example 5

Preparation of 2-(1H-Indazol-4-yl)-4-morpholin-4-yl-thieno[3,2-d]pyrimidine-6-carbaldehyde (71)

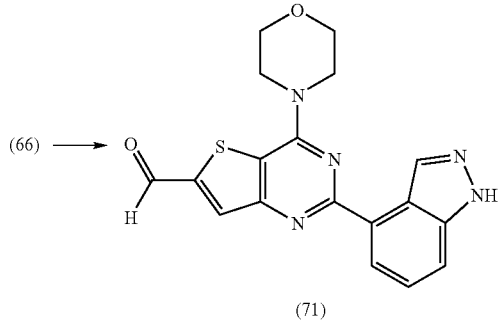

A mixture of 2-chloro-4-morpholin-4-yl-thieno[3,2-d]pyrimidine-6-carbaldehyde (66) (100 mg, 0.35 mmol), 4-(4,4,5,5-tetramethyl-[1,3,2]dioxaborolan-2-yl)-1H-indazole (70) (95 mg, 0.39 mmol) and sodium carbonate (112 mg) were suspended in toluene (2.5 mL), ethanol (1.5 mL) and water (0.7 mL). To this was added bis(triphenylphosphine)palladium(II) chloride (13.5 mg) and the reaction vessel was flushed with argon. The reaction mixture was microwaved at 120° C. for 1 hour and then partitioned between dichloromethane and water, the organic layer was washed with brine, dried over magnesium sulfate, filtered and evaporated in vacuo. The resulting residue was purified using flash chromatography to yield the title compound 71 (97 mg).

Reference Example 6

Preparation of 2-(1H-Indazol-4-yl)-6-(4-methyl-piperazin-1-ylmethyl)-4-morpholin-4-yl-thieno[3,2-d]pyrimidine (59)

To a mixture of 2-(1H-Indazol-4-yl)-4-morpholin-4-yl-thieno[3,2-d]pyrimidine-6-carbaldehyde (91 mg, 0.26 mmol), 1-methylpiperazine (34 mg, 0.36 mmol) and acetic acid (15 uL) in 1,2-dichloroethane (2 mL) was added sodium triacetoxyborohydride (60 mg, 0.28 mmol). The reaction mixture was stirred at room temperature overnight and then basified (NaHCO$_3$, saturated), diluted with dichloromethane, washed with brine. Organic layer was separated, dried (MgSO$_4$), filtered and evaporated in vacuo. The residue was purified using flash chromatography to give the title compound (33 mg).

The following compounds were prepared by analogy with the procedure described above.

2-{4-[2-(1H-Indazol-4-yl)-4-morpholin-4-yl-thieno[3,2-d]pyrimidin-6-ylmethyl]-piperazin-1-yl}-ethanol using 1-(2-hydroxyethyl)piperazine.

$^1$H NMR (400 MHz, d$_6$-DMSO) 2.40 (br m, 2H), 2.42-2.52 (b, 8H, under DMSO peak), 3.48 (q, 2H, J=6.0 Hz), 3.82-3.86 (m, 6H), 3.98-4.01 (m, 4H), 4.34 (br s, 1H), 7.44-7.48 (m, 2H), 7.65 (d, 1H, J=8.3 Hz), 8.21 (d, 1H, J=6.8 Hz), 8.87 (s, 1H), 13.15 (brs, 1H); MS (ESI$^+$) 480.1 (MH$^+$).

4-[2-(1H-Indazol-4-yl)-4-morpholin-4-yl-thieno[3,2-d]pyrimidin-6-ylmethyl]-piperazine-1-sulfonic acid dimethylamide using piperazine-1-sulfonic acid dimethylamide.

$^1$H NMR (400 MHz, CDCl$_3$) 2.63-2.66 (m, 4H), 2.84 (s, 6H), 3.31-3.34 (m, 4H), 3.89 (s 2H), 3.92-3.94 (m, 4H), 4.08-4.11 (m, 4H), 7.39 (s, 1H), 7.51 (t, 1H, J=8.1 Hz), 7.60 (d, 1H, J=8.1 Hz), 8.28 (d, 1H, J=6.7 Hz), 9.02 (s, 1H), 10.12 (br s 1H); MS (ESI$^+$) 543.1 (MH$^+$).

Example 6

Further Compounds of the Invention

The following compound were prepared by analogy with the procedure described in Reference Example 6:

176: 1-{3-[6-(4-Methyl-piperazin-1-ylmethyl)-4-morpholin-4-yl-thieno[3,2-d]pyrimidin-2-yl]-phenyl}-ethanol.

As for 59, except treatment of 3-[6-(4-methyl-piperazin-1-ylmethyl)-4-morpholin-4-yl-thieno[3,2-d]pyrimidin-2-yl]-benzaldehyde with methyl magnesium bromide in THF/ether yielded the title compound.

$^1$H NMR (400 MHz, CDCl$_3$): 1.49 (d, J=6.5, 3H), 2.10 (d, J=1.7 Hz, 1H), 2.25 (s, 3H), 2.46 (br s, 4H), 2.54 (s, br, 4H), 3.74 (s, 2H), 3.82 (t, J=4.8 Hz, 4H), 3.98 (t, J=4.8, 4H), 4.94 (q, J=6.4 Hz, 1H), 7.23 (s, 1H), 7.35-7.42 (m, 2H), 8.27 (m, 1H), 8.35 (s, 1H); MS (ESI$^+$) 454.27 (MH$^+$).

177: 3-[6-(4-Methyl-piperazin-1-ylmethyl)-4-morpholin-4-yl-thieno[3,2-d]pyrimidin-2-yl]-phenyl}-methanol.

As for 59, except treatment of 3-[6-(4-methyl-piperazin-1-ylmethyl)-4-morpholin-4-yl-thieno[3,2-d]pyrimidin-2-yl]-benzaldehyde with sodium borohydride in ethanol at room temperature yielded the title compound.

$^1$H NMR (400 MHz, CDCl$_3$): 2.25 (s, 3H), 2.47 (s, 4H), 2.54 (s, 4H), 3.75 (s, 2H), 3.80 (t, J=4.8 Hz, 4H), 3.98 (t, J=4.8 Hz, 4H), 4.71 (s, 2H), 7.23 (m, 1H), 7.38 (m, 2H), 8.28 (m, 1H), 8.34 (s, 1H); MS (ESI$^+$) 440.23 (MH$^+$).

178: 6-(4-Methyl-piperazin-1-ylmethyl)-4-morpholin-4-yl-2-(1H-pyrazol-4-yl)-thieno[3,2-d]pyrimidine.

As for compound 59.

$^1$H NMR (400 MHz, d$_6$-DMSO): 2.15 (s, 3H), 2.41 (m, 8H), 3.77 (m, 4H), 3.85 (s, 2H), 3.92 (m, 4H), 7.26 (s, 1H), 8.31 (br s, 1H), 13.05 (br s, 1H); MS (ESI$^+$) 400.21 (MH$^+$).

Reference Example 7

2-chloro-6-(4-methyl-piperazin-1-yl methyl)-4-morpholin-4-yl-thieno[3,2-d]pyrimidine (72)

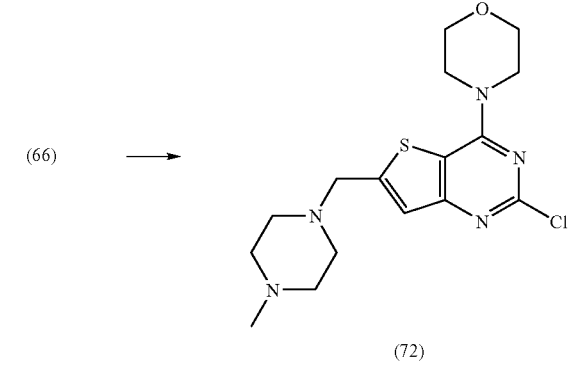

To a mixture of 2-chloro-4-morpholin-4-yl-thieno[3,2-d]pyrimidine-6-carbaldehyde (66) (147 mg, 0.52 mmol), 1-methyl-piperazine (1.5 eq., 87 µL) and acetic acid (1.05 eq., 32 µL) in 1,2-dichloroethane (3 mL) was added sodium triacetoxyborohydride (1.1 eq., 121 mg) and then stirred at room temperature overnight. The reaction mixture was diluted with dichloromethane, washed with a saturated solution of sodium hydrogen carbonate, brine, separated and dried (MgSO$_4$). The crude product was evaporated in vacuo and purified by chromatography to give the title compound 72 as an off-white crystalline solid (51 mg, 45%).

Example 11

Biological Testing

Compounds of the invention, prepared as described in the preceding Examples, were submitted to the following series of biological assays:

(i) PI3K Biochemical Screening

Compound inhibition of PI3K was determined in a radiometric assay using purified, recombinant enzyme and ATP at a concentration of 1 uM. All compounds were serially diluted in 100% DMSO. The kinase reaction was incubated for 1 hour at room temperature, and the reaction was terminated by the addition of PBS. IC$_{50}$ values were subsequently determined using sigmoidal dose-response curve fit (variable slope). All of the compounds exemplified had an IC$_{50}$ against PI3K of 50 uM or less.

(ii) Cellular Proliferation Inhibition

Cells were seeded at optimal density in a 96 well plate and incubated for 4 days in the presence of test compound. Alamar Blue™ was subsequently added to the assay medium, and cells were incubated for 6 hours before reading at 544 nm excitation, 590 nm emission. EC$_{50}$ values were calculated using a sigmoidal dose response curve fit. All the compounds tested had an EC$_{50}$s of 50 uM or less in the range of cell lines utilized.

(iii) Caco-2 Permeability

Caco-2 cells were seeded onto Millipore Multiscreen plates at 1×10$^5$ cells/cm$^2$, and were cultured for 20 days. Assessment of compound permeability was subsequently conducted. The compounds were applied to the apical surface (A) of cell monolayers and compound permeation into the basolateral (B) compartment was measured. This was performed in the reverse direction (B–A) to investigate active transport. A permeability coefficient value, P$_{app}$, for each compound, a measure of the rate of permeation of the compound across the membrane, was calculated. Compounds were grouped into low (P$_{app}$</=1.0×10$^6$ cm/s) or high (P$_{app}$>/= 1.0×10$^6$ cm/s) absorption potential based on comparison with control compounds with established human absorption.

For assessment of a compound's ability to undergo active efflux, the ratio of basolateral (B) to apical (A) transport compared with A to B was determined. Values of B–A/A–B>/=1.0 indicated the occurrence of active cellular efflux. All of the compounds tested through the Caco-2 permeability screen had P$_{app}$ values>/=1.0×10$^6$ cm/s. One compound assessed through the bidirectional assay, PI540, had an B–A/A–B asymmetry index of less than 1.0, indicating that the compound does not undergo active cellular efflux.

(iv) Hepatocyte Clearance

Suspensions of cryopreserved human hepatocytes were used. Incubations were performed at compound concentration of 1 mM or 3 μM at a cell density of 0.5×10$^6$ viable cells/mL. The final DMSO concentration in the incubation was 0.25%. Control incubations were also performed in the absence of cells to reveal any non-enzymatic degradation. Duplicate samples (50 μL) were removed from the incubation mixture at 0, 5, 10, 20, 40 and 60 minutes (control sample at 60 minutes only) and added to methanol—containing internal standard (100 μL)—to terminate the reaction. Tolbutamide, 7-hydroxycoumarin, and testosterone were used as control compounds. Samples were centrifuged and the supernatants at each time point pooled for analysis by LC-MSMS. From a plot of ln peak area ratio (parent compound peak area/internal standard peak area) against time, intrinsic clearance (CL$_{int}$) was calculated as follows: CL$_{int}$ (μl/min/million cells)=V×k, where k is the elimination rate constant, obtained from the gradient of ln concentration plotted against time; V is a volume term derived from the incubation volume and is expressed as uL 10$^6$ cells$^{-1}$.

Compounds were classified with low (CL</=4.6 μL/min/10$^6$ cells), medium (CL>/=4.6; </=25.2 μl/min/10$^6$ cells) and high (>/=25.2 μl/min/10$^6$ cells) clearance. The majority of the tested compounds of the invention were determined to have low hepatocyte clearance.

(v) Cytochrome P450 Inhibition

Compounds of the invention were screened against five CYP450 targets (1A2, 2C9, 2C19, 2D6, 3A4) at 10 concentrations in duplicate, with a top concentration of 100 uM being used. Standard inhibitors (furafylline, sulfaphenazole, tranylcypromine, quinidine, ketoconazole) were used as controls. Plates were read using a BMG LabTechnologies PolarStar in fluorescence mode. The majority of the tested compounds assessed in this assay displayed weak activity (IC$_{50}$>/=5 uM) against all isoforms of CYP450.

(vi) Cytochrome P450 Induction

Freshly isolated human hepatocytes from a single donor were cultured for 48 hours prior to addition of test compound at three concentrations and were incubated for 72 hours. Probe substrates for CYP3A4 and CYP1A2 were added for 30 minutes and 1 hour before the end of the incubation. At 72 hours, cells and media were removed and the extent of metabolism of each probe substrate quantified by LC-MS/MS. The experiment was controlled by using inducers of the individual P450s incubated at one concentration in triplicate. The compounds of the invention assessed in this assay showed negligible effects on induction of cytochrome P450 enzymes.

(vii) Plasma Protein Binding

Solutions of test compound (5 um, 0.5% final DMSO concentration) were prepared in buffer and 10% plasma (v/v in buffer). A 96 well HT dialysis plate was assembled so that each well was divided in two by a semi-permeable cellulose membrane. The buffer solution was added to one side of the membrane and the plasma solution to the other side; incubations were then conducted at 37° C. over 2 hours in triplicate. The cells were subsequently emptied, and the solutions for each batch of compounds were combined into two groups (plasma-free and plasma-containing) then analysed by LC-MSMS using two sets of calibration standards for plasma-free (6 points) and plasma-containing solutions (7 points). The fraction unbound value for each compound was calculated: highly protein bound compounds (>/=90% bound) had an Fu</=0.1. The compounds of the invention assessed in this assay had Fu values>/=0.1.

(viii) hERG Channel Blockage

Compounds of the invention were evaluated for their ability to modulate rubidium efflux from HEK-294 cells stably expressing hERG potassium channels using established flux methodology. Cells were prepared in medium containing RbCl and were plated into 96-well plates and grown overnight to form monolayers. The efflux experiment was initiated by aspirating the media and washing each well with 3×100 μL of pre-incubation buffer (containing low [K$^+$]) at room temperature. Following the final aspiration, 50 μL of working stock (2×) compound was added to each well and incubated at room temperature for 10 minutes. 50 μL of stimulation buffer (containing high [K+]) was then added to each well giving the final test compound concentrations. Cell plates were then incubated at room temperature for a further 10 minutes. 80 μL of supernatant from each well was then transferred to equivalent wells of a 96-well plate and analysed via atomic emission spectroscopy. Compounds were screened as 10 pt duplicate $IC_{50}$ curves, n=2, from a top concentration of 100 μM.

Example 12

Tablet Composition

Tablets, each weighing 0.15 g and containing 25 mg of a compound of the invention were manufactured as follows:

Composition for 10,000 Tablets

Active compound (250 g)

Lactose (800 g)

Corn starch (415 g)

Talc powder (30 g)

Magnesium stearate (5 g)

The active compound, lactose and half of the corn starch were mixed. The mixture was then forced through a sieve 0.5 mm mesh size. Corn starch (10 g) is suspended in warm water (90 ml). The resulting paste was used to granulate the powder. The granulate was dried and broken up into small fragments on a sieve of 1.4 mm mesh size. The remaining quantity of starch, talc and magnesium was added, carefully mixed and processed into tablets.

Example 13

Injectable Formulation

| Formulation A | |
|---|---|
| Active compound | 200 mg |
| Hydrochloric Acid Solution 0.1M or Sodium Hydroxide Solution 0.1M q.s. to pH | 4.0 to 7.0 |
| Sterile water q.s. to | 10 ml |

The compound of the invention was dissolved in most of the water (35° 40° C.) and the pH adjusted to between 4.0 and 7.0 with the hydrochloric acid or the sodium hydroxide as appropriate. The batch was then made up to volume with water and filtered through a sterile micropore filter into a sterile 10 ml amber glass vial (type 1) and sealed with sterile closures and overseals.

| Formulation B | |
|---|---|
| Active Compound | 125 mg |
| Sterile, Pyrogen-free, pH 7 Phosphate Buffer, q.s. to | 25 ml |
| Active compound | 200 mg |
| Benzyl Alcohol | 0.10 g |

| -continued | |
|---|---|
| Formulation B | |
| Glycofurol 75 | 1.45 g |
| Water for injection q.s to | 3.00 ml |

The active compound was dissolved in the glycofurol. The benzyl alcohol was then added and dissolved, and water added to 3 ml. The mixture was then filtered through a sterile micropore filter and sealed in sterile 3 ml glass vials (type 1).

Example 17

Syrup Formulation

| Active compound | 250 mg |
|---|---|
| Sorbitol Solution | 1.50 g |
| Glycerol | 2.00 g |
| Sodium benzoate | 0.005 g |
| Flavour | 0.0125 ml |
| Purified Water q.s. to | 5.00 ml |

The compound of the invention was dissolved in a mixture of the glycerol and most of the purified water. An aqueous solution of the sodium benzoate was then added to the solution, followed by addition of the sorbital solution and finally the flavour. The volume was made up with purified water and mixed well.

The invention claimed is:

1. A compound which is a fused pyrimidine of formula (I):

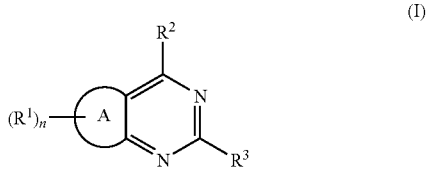

(I)

wherein

A represents a thiophene or furan ring;

n is 1 or 2;

$R^1$ is a group of formula:

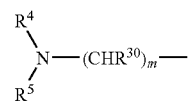

wherein m is 0 or 1;

$R^{30}$ is H or $C_1$-$C_6$ alkyl;

$R^4$ and $R^5$ form, together with the N atom to which they are attached, a 5- or 6-membered saturated N-containing heterocyclic group which includes 0 or 1 additional heteroatoms selected from N, S and O, which may be fused to a benzene ring and which is unsubstituted or substituted; or one of $R^4$ and $R^5$ is alkyl and the other is a 5- or 6-membered saturated N-containing heterocyclic group as defined above or an alkyl group which is substituted by a 5- or 6-membered saturated N-containing heterocyclic group as defined above;

R² is selected from:

(a)

wherein R⁶ and R⁷ form, together with the nitrogen atom to which they are attached, a morpholine, thiomorpholine, piperidine, piperazine, oxazepane or thiazepane group which is unsubstituted or substituted; and

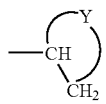
(b)

wherein Y is a $C_2$-$C_4$ alkylene chain which contains, between constituent carbon atoms of the chain and/or at one or both ends of the chain, 1 or 2 heteroatoms selected from O, N and S, and which is unsubstituted or substituted;

and R³ is:

a group of the following formula:

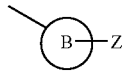

wherein B is a phenyl ring which is unsubstituted or substituted and Z is selected from H, —OR, —SR, CH₂OR, —CO₂R, CF₂OH, CH(CF₃)OH, C(CF₃)₂OH, —(CH₂)$_q$OR, —(CH₂)$_q$NR₂, —C(O)N(R)₂, —NR₂, —NRC(O)R, —S(O)$_{mm}$N(R)₂, —OC(O)R, OC(O)N(R)₂, —NRS(O)$_{mm}$R, —NRC(O)N(R)₂, CN, halogen and —NO₂, wherein each R is independently selected from H, $C_1$-$C_6$ alkyl, $C_3$-$C_{10}$ cycloalkyl and a 5- to 12-membered aryl or heteroaryl group, the group being unsubstituted or substituted, m$\underline{m}$ is 1 or 2 and q is 0, 1 or 2;

or a pharmaceutically acceptable salt thereof.

2. A compound according to claim 1 wherein the fused pyrimidine is of formula (Ia):

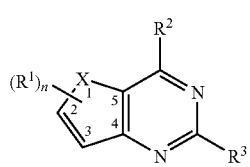
(Ia)

wherein X is O or S and R¹, R², R³ and n are as defined in claim 1.

3. A compound according to claim 1 wherein the fused pyrimidine is of formula (Ib):

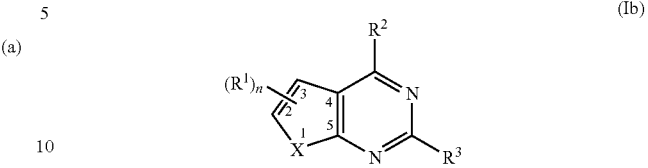
(Ib)

wherein X is O or S and R¹, R², R³ and n are as defined in claim 1.

4. A compound according to claim 1 which is selected from:
  3-(4-Morpholin-4-yl-6-morpholin-4-ylmethyl-thieno[3,2-d]pyrimidin-2-yl)-phenol;
  3-(4-Morpholin-4-yl-6-pyrrolidin-1-ylmethyl-thieno[3,2-d]pyrimidin-2-yl)-phenol;
  3-[6-(4-Methyl-piperazin-1-ylmethyl)-4-morpholin-4-yl-thieno[3,2-d]pyrimidin-2-yl]-phenol;
  3-[6-(6,7-Dimethoxy-3,4-dihydro-1H-isoquinolin-2-ylmethyl)-4-morpholin-4-yl-thieno[3,2-d]pyrimidin-2-yl]-phenol;
  3-(6-[1,4']Bipiperidinyl-1'-ylmethyl-4-morpholin-4-yl-thieno[3,2-d]pyrimidin-2-yl)-phenol;
  3-[4-Morpholin-4-yl-6-(4-pyrimidin-2-yl-piperazin-1-ylmethyl)-thieno[3,2-d]pyrimidin-2-yl]-phenol;
  3-[6-(4-Cyclohexylmethyl-piperazin-1-ylmethyl)-4-morpholin-4-yl-thieno[3,2-d]pyrimidin-2-yl]-phenol;
  4-[2-(3-Hydroxy-phenyl)-4-morpholin-4-yl-thieno[3,2-d]pyrimidin-6-ylmethyl]-piperazine-1-carboxylic acid tert-butyl ester;
  3-(4-Morpholin-4-yl-6-piperazin-1-ylmethyl-thieno[3,2-d]pyrimidin-2-yl)-phenol trifluoroacetic acid salt;
  3-{6-[4-(2-Methoxy-ethyl)-piperazin-1-ylmethyl]-4-morpholin-4-yl-thieno[3,2-d]pyrimidin-2-yl}-phenol;
  3-[6-(4-Methyl-[1,4]diazepan-1-ylmethyl)-4-morpholin-4-yl-thieno[3,2-d]pyrimidin-2-yl]-phenol;
  {4-[2-(3-Hydroxy-phenyl)-4-morpholin-4-yl-thieno[3,2-d]pyrimidin-6-ylmethyl]-piperazin-1-yl}-acetic acid ethyl ester;
  1-{4-[2-(3-Hydroxy-phenyl)-4-morpholin-4-yl-thieno[3,2-d]pyrimidin-6-ylmethyl]-piperazin-1-yl}-ethanone;
  3-{6-[4-(2-Hydroxy-ethyl)-piperazin-1-ylmethyl]-4-morpholin-4-yl-thieno[3,2-d]pyrimidin-2-yl}-phenol;
  3-(4-Morpholin-4-yl-6-thiomorpholin-4-ylmethyl-thieno[3,2-d]pyrimidin-2-yl)-phenol;
  3-[6-(4-Ethyl-piperazin-1-ylmethyl)-4-morpholin-4-yl-thieno[3,2-d]pyrimidin-2-yl]-phenol;
  3-(6-{[Methyl-(1-methyl-piperidin-4-yl)-amino]-methyl}-4-morpholin-4-yl-thieno[3,2-d]pyrimidin-2-yl)-phenol;
  3-[6-(4-Dimethylamino-piperidin-1-ylmethyl)-4-morpholin-4-yl-thieno[3,2-d]pyrimidin-2-yl]-phenol;
  4-[2-(3-Hydroxy-phenyl)-4-morpholin-4-yl-thieno[3,2-d]pyrimidin-6-ylmethyl]-piperazin-2-one;
  3-[6-(4-Methanesulfonyl-piperazin-1-ylmethyl)-4-morpholin-4-yl-thieno[3,2-d]pyrimidin-2-yl]-phenol;
  {4-[2-(3-Hydroxy-phenyl)-4-morpholin-4-yl-thieno[3,2-d]pyrimidin-6-ylmethyl]-piperazin-1-yl}-acetonitrile;
  3-[4-Morpholin-4-yl-6-(4-morpholin-4-yl-piperidin-1-ylmethyl)-thieno[3,2-d]pyrimidin-2-yl]-phenol;
  3-[6-(4-Amino-piperidin-1-ylmethyl)-4-morpholin-4-yl-thieno[3,2-d]pyrimidin-2-yl]-phenol;

3-[6-(3-Dimethylamino-pyrrolidin-1-ylmethyl)-4-morpholin-4-yl-thieno[3,2-d]pyrimidin-2-yl]-phenol;

1-[2-(3-Hydroxy-phenyl)-4-morpholin-4-yl-thieno[3,2-d]pyrimidin-6-ylmethyl]-4-morpholin-4-ylmethyl-piperidin-4-ol;

4-[2-(3-Hydroxy-phenyl)-4-morpholin-4-yl-thieno[3,2-d]pyrimidin-6-ylmethyl]-piperazine-1-carboxylic acid ethylamide;

N-{1-[2-(3-Hydroxy-phenyl)-4-morpholin-4-yl-thieno[3,2-d]pyrimidin-6-ylmethyl]-piperidin-4-yl}-methanesulfonamide;

1-{4-[2-(3-Hydroxy-phenyl)-4-morpholin-4-yl-thieno[3,2-d]pyrimidin-6-ylmethyl]-piperazin-1-yl}-2-methoxy-ethanone;

N-{1-[2-(3-Hydroxy-phenyl)-4-morpholin-4-yl-thieno[3,2-d]pyrimidin-6-ylmethyl]-piperidin-4-yl}-acetamide;

4-[2-(3-Hydroxy-phenyl)-4-morpholin-4-yl-thieno[3,2-d]pyrimidin-6-ylmethyl]-piperazine-1-carboxylic acid dimethylamide;

1-[2-(3-Hydroxy-phenyl)-4-morpholin-4-yl-thieno[3,2-d]pyrimidin-6-ylmethyl]-piperidin-4-ol;

3-[6-1,1-Dioxo-thiomorpholin-4-ylmethyl)-4-morpholin-4-yl-thieno[3,2-d]pyrimidin-2-yl]-phenol 4-[2-(3-Hydroxy-phenyl)-4-morpholin-4-yl-thieno[3,2-d]pyrimidin-6-ylmethyl]-piperazine-1-sulfonic acid dimethylamide;

3-(6-{4-[(2-Methoxy-ethyl)-methyl-amino]-piperidin-1-ylmethyl}-4-morpholin-4-yl-thieno[3,2-d]pyrimidin-2-yl)-phenol;

1-[2-(3-Hydroxy-phenyl)-4-morpholin-4-yl-thieno[3,2-d]pyrimidin-6-ylmethyl]-pyrrolidin-3-ol;

(R,S)-3-[6-(2-Dimethylaminomethyl-pyrrolidin-1-ylmethyl)-4-morpholin-4-yl-thieno[3,2-d]pyrimidin-2-yl]-phenol;

(R,S)-3-(6-{[Methyl-(1-methyl-pyrrolidin-2-ylmethyl)-amino]-methyl}-4-morpholin-4-yl-thieno[3,2-d]pyrimidin-2-yl)-phenol;

1-[2-(3-Hydroxy-phenyl)-4-morpholin-4-yl-thieno[3,2-d]pyrimidin-6-ylmethyl]-piperidine-4-carboxylic acid amide;

2-{4-[2-(3-Hydroxy-phenyl)-4-morpholin-4-yl-thieno[3,2-d]pyrimidin-6-ylmethyl]-piperazin-1-yl}-N,N-dimethyl-acetamide;

3-(6-{[Methyl-(1-methyl-pyrrolidin-3-yl)-amino]-methyl}-4-morpholin-4-yl-thieno[3,2-d]pyrimidin-2-yl)-phenol;

2-Dimethylamino-1-{4-[2-(3-hydroxy-phenyl)-4-morpholin-4-yl-thieno[3,2-d]pyrimidin-6-ylmethyl]-piperazin-1-yl}-ethanone;

3-[6-((3R,5S)-3,5-Dimethyl-piperazin-1-ylmethyl)-4-morpholin-4-yl-thieno[3,2-d]pyrimidin-2-yl]-phenol;

3-[6-((3R,5S)-4-Methanesulfonyl-3,5-dimethyl-piperazin-1-ylmethyl)-4-morpholin-4-yl-thieno[3,2-d]pyrimidin-2-yl]-phenol;

1-{(2R,6S)-4-[2-(3-Hydroxy-phenyl)-4-morpholin-4-yl-thieno[3,2-d]pyrimidin-6-ylmethyl]-2,6-dimethyl-piperazin-1-yl}-ethanone;

3-{6-[4-(3-Dimethylamino-propane-1-sulfonyl)-piperazin-1-ylmethyl]-4-morpholin-4-yl-thieno[3,2-d]pyrimidin-2-yl}-phenol;

3-[6-(4-Methoxy-piperidin-1-ylmethyl)-4-morpholin-4-yl-thieno[3,2-d]pyrimidin-2-yl]-phenol;

3-{4-Morpholin-4-yl-6-[4-(3-morpholin-4-yl-propane-1-sulfonyl)-piperazin-1-ylmethyl]-thieno[3,2-d]pyrimidin-2-yl}-phenol;

{4-[2-(3-Hydroxy-phenyl)-4-morpholin-4-yl-thieno[3,2-d]pyrimidin-6-ylmethyl]-piperazin-1-yl}-morpholin-4-yl-methanone;

4-[2-(3-Hydroxy-phenyl)-4-morpholin-4-yl-thieno[3,2-d]pyrimidin-6-ylmethyl]-piperazine-1-carboxylic acid (2-methoxy-ethyl)-methyl-amide;

1-{3-[6-(4-Methyl-piperazin-1-ylmethyl)-4-morpholin-4-yl-thieno[3,2-d]pyrimidin-2-yl]-phenyl}-ethanol;

3-[6-(4-Methyl-piperazin-1-ylmethyl)-4-morpholin-4-yl-thieno[3,2-d]pyrimidin-2-yl]-phenyl}-methanol;

2-Chloro-5-[6-(4-methyl-piperazin-1-ylmethyl)-4-morpholin-4-yl-thieno[3,2-d]pyrimidin-2-yl]-phenol;

2,3-Difluoro-5-[6-(4-methyl-piperazin-1-ylmethyl)-4-morpholin-4-yl-thieno[3,2-d]pyrimidin-2-yl]-phenol;

4-Fluoro-3-[6-(4-methyl-piperazin-1-ylmethyl)-4-morpholin-4-yl-thieno[3,2-d]pyrimidin-2-yl]-phenol; and 2-(1H-Indazol-6-yl)-6-(4-methyl-piperazin-1-ylmethyl)-4-morpholin-4-yl-thieno[3,2-d]pyrimidin-2-yl]-phenol;

and the pharmaceutically acceptable salts of the above-mentioned free compounds.

5. A process for producing a compound as defined in claim 1 wherein m is 1, which process comprises:

(a) treating a compound of formula (II):

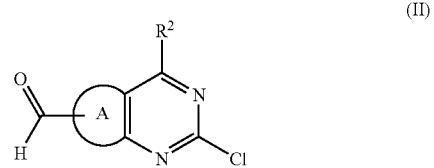

wherein A and $R^2$ are as defined in claim 1, with a boronic acid or ester thereof of formula $R^3B(OR^{15})_2$, in which $R^3$ is as defined above and each $R^{15}$ is H or $C_1$-$C_6$ alkyl or the two groups $OR^{15}$ form, together with the boron atom to which they are attached, a pinacolato boronate ester, in the presence of a Pd catalyst; and treating the resulting compound of formula (III):

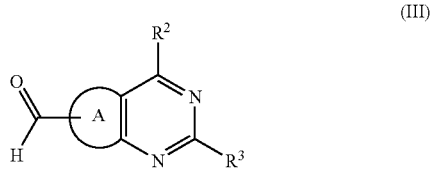

wherein A, $R^2$ and $R^3$ are as defined above, with an amine of formula $NHR^4R^5$ wherein $R^4$ and $R^5$ are as defined in claim 1, in the presence of a suitable reducing agent; or (b) treating a compound of formula (II) as defined above with an amine of formula $NHR^4R^5$ wherein $R^4$ and $R^5$ are as defined above, in the presence of a suitable reducing agent;

and treating the resulting compound of formula (IV):

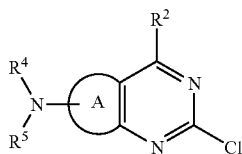
(IV)

wherein A, R⁴ and R⁵ are as defined above, with a boronic acid or ester thereof of formula $R^3B(OR^{15})_2$, in which $R^3$ is as defined above and each $R^{15}$ is H or $C_1$-$C_6$ alkyl or the two groups $OR^{15}$ form, together with the boron atom to which they are attached, a pinacolato boronate ester group, in the presence of a Pd catalyst, and (c) optionally converting the resulting compound of formula (I) into a pharmaceutically acceptable salt thereof.

6. A process for producing a compound of formula (I) as defined in claim 1, in which m is 1 and $R^3$ is a 3- or 4-hydroxyphenyl group, which process comprises:

(a) treating a compound of formula (V):

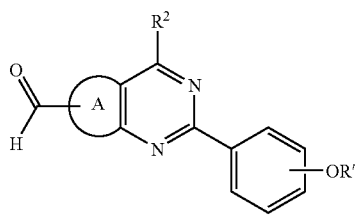
(V)

wherein OR' is bonded at position 3 or 4 of the phenyl ring to which it is attached, R' is a hydroxy protecting group and $R^2$ is as defined in claim 1, with an amine of formula $NHR^4R^5$ wherein $R^4$ and $R^5$ are as defined in claim 1, in the presence of a suitable reducing agent; and (b) removing the hydroxy protecting group, and (c) optionally converting the resulting compound of formula (I) into a pharmaceutically acceptable salt thereof.

7. A process for producing a compound as defined in claim 1 wherein m is 0, which process comprises treating a compound of formula (XIV):

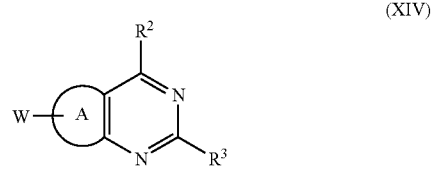
(XIV)

wherein A, $R^2$ and $R^3$ are as defined in claim 1 and W is a halo group selected from Br and I, with an amine of formula $NHR^4R^5$ in which $R^4$ and $R^5$ are as defined in claim 1, in the presence of a palladium catalyst, and optionally converting the resulting compound of formula (I) into a pharmaceutically acceptable salt thereof.

8. A process according to claim 5 which comprises converting the resulting compound of formula (I) into a pharmaceutically acceptable salt thereof.

9. A process according to claim 6 which comprises converting the resulting compound of formula (I) into a pharmaceutically acceptable salt thereof.

10. A process according to claim 7 which comprises converting the resulting compound of formula (I) into a pharmaceutically acceptable salt thereof.

11. A pharmaceutical composition which comprises a pharmaceutically acceptable carrier or diluent and, as an active ingredient, a compound as claimed in claim 1.

* * * * *

UNITED STATES PATENT AND TRADEMARK OFFICE
CERTIFICATE OF CORRECTION

| | | |
|---|---|---|
| PATENT NO. | : 7,872,003 B2 | Page 1 of 1 |
| APPLICATION NO. | : 11/893625 | |
| DATED | : January 18, 2011 | |
| INVENTOR(S) | : Stephen J. Shuttleworth et al. | |

It is certified that error appears in the above-identified patent and that said Letters Patent is hereby corrected as shown below:

In claim 4, at Column 46, line 34
*Replace*
tert-butyl ester;
*With*
*tert*-butyl ester;

In claim 4, at Column 47, line 33
*Replace*
(R,S)-3-[6-(2-Dimethyl . . . .
*With*
(*R*,*S*)-3-[6-(2-Dimethyl . . . .

In claim 4, at Column 47, line 36
*Replace*
(R,S)-3-[6-{[Methyl . . . .
*With*
(*R*,*S*)-3-[6-{[Methyl . . . .

Signed and Sealed this
Thirty-first Day of January, 2012

David J. Kappos
*Director of the United States Patent and Trademark Office*